US012629009B2

(12) United States Patent
    Kodama

(10) Patent No.: US 12,629,009 B2
(45) Date of Patent: May 19, 2026

(54) MEDICAL DEVICE

(71) Applicant: JAPAN LIFELINE CO., LTD., Tokyo (JP)

(72) Inventor: Yuki Kodama, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 472 days.

(21) Appl. No.: 18/026,891

(22) PCT Filed: Oct. 20, 2020

(86) PCT No.: PCT/JP2020/039464
     § 371 (c)(1),
     (2) Date: Mar. 17, 2023

(87) PCT Pub. No.: WO2022/085092
     PCT Pub. Date: Apr. 28, 2022

(65) Prior Publication Data
     US 2023/0329535 A1    Oct. 19, 2023

(51) Int. Cl.
     *A61B 1/00*      (2006.01)
     *A61B 1/005*     (2006.01)
     *A61B 1/018*     (2006.01)
(52) U.S. Cl.
     CPC .......... *A61B 1/0057* (2013.01); *A61B 1/0052* (2013.01); *A61B 1/018* (2013.01)
(58) Field of Classification Search
     CPC ..... A61B 1/0008; A61B 1/0055; A61B 1/012; A61B 1/0057; A61B 1/0052; A61B 1/018
     See application file for complete search history.

(56) References Cited

U.S. PATENT DOCUMENTS

2006/0235273 A1* 10/2006 Moriyama ......... A61B 1/00188
                                                        600/113
2015/0359416 A1   12/2015 Simchony et al.
                         (Continued)

FOREIGN PATENT DOCUMENTS

CN       104853801 A      8/2015
CN       109068942 A     12/2018
                  (Continued)

OTHER PUBLICATIONS

Chinese Office Action issued for corresponding Chinese Patent Application No. 202080106360.3 dated Sep. 18, 2024 and its english translation; pp. 1-27.
                  (Continued)

*Primary Examiner* — Anh Tuan T Nguyen
*Assistant Examiner* — Rynae E Boler
(74) *Attorney, Agent, or Firm* — MUNCY, GEISSLER, OLDS & LOWE, P.C.

(57)                ABSTRACT
A medical device is configured such that a distal end of an operation wire is securely fixed to a distal end of a shaft, enabling smooth distal end deflection operation. The medical device includes: a shaft that includes a distal end flexible portion and in which working lumens and wire lumens are formed; a distal end tip disposed on a distal end side of the shaft and in which distal end working lumens in communication with the working lumens are formed; an intermediate member disposed between the shaft and the distal end tip and including a main through-hole that is formed to secure communication paths with the working lumens and the distal end working lumens and surround the communication paths, and sub-through-holes that are formed to correspond to the positions in which the wire lumens are formed.

8 Claims, 17 Drawing Sheets

(56)     References Cited

U.S. PATENT DOCUMENTS

| | | | |
|---|---|---|---|
| 2019/0254504 A1* | 8/2019 | Ide | A61B 1/018 |
| 2019/0328212 A1* | 10/2019 | Nakaji | A61B 1/00071 |
| 2020/0187765 A1* | 6/2020 | Ide | G02B 23/2469 |
| 2021/0106788 A1* | 4/2021 | Brown | A61M 25/06 |

FOREIGN PATENT DOCUMENTS

| | | |
|---|---|---|
| CN | 110167416 A | 8/2019 |
| JP | 6-269421 A | 9/1994 |
| JP | 2005305185 A | 11/2005 |
| JP | 2009-530051 A | 8/2009 |
| JP | 2014000265 A | 1/2014 |
| JP | 2014087386 A | 5/2014 |
| JP | 2015-167573 A | 9/2015 |
| WO | WO2020/096035 A1 | 5/2020 |

OTHER PUBLICATIONS

Office Action for CN Application No. 2020801063603, dated Feb. 25, 2025 and it's English translation is attached (34 pages).

* cited by examiner

MEDICAL DEVICE

TECHNICAL FIELD

The present invention relates to a medical device including a distal end deflection-operable shaft.

BACKGROUND ART

Conventionally, an endoscope equipped with a shaft to be inserted into the body and an operation handle has been known as a small endoscope used for diagnostic treatment of biliary ducts and pancreatic ducts via a duodenoscope (see Patent Document 1 described below).

In the endoscope described in Patent Document 1, the orientation of a distal end of a shaft inserted into the body can be changed (deflected) by operating a handle disposed outside the body.

Specifically, by rotating an operation knob attached to the handle and thereby pulling a tail end of an operation wire, a distal end portion of the shaft to which a distal end of the operation wire is fixed is warped to deflect the distal end of the shaft.

Two operation knobs (inner knob and outer knob) are attached to the handle of the endoscope described in Patent Document 1, and tail ends of two operation wires are respectively fixed to the knobs.

The distal end of the operation wire is welded to an inner circumferential surface of a cylindrical metal member (X-ray opaque marker band) mounted on the outer circumference of the distal end portion of the shaft and is thereby fixed via the metal member to the distal end portion of the shaft (see FIG. 6A in the same document).

CITATION LIST

Patent Literature

Patent Document 1: JP 2009-530051 A

SUMMARY OF INVENTION

Technical Problem

However, in a case where the distal end of the operation wire is fixed via a cylindrical metal member as in the endoscope described in Patent Document 1, body tissue and the like may be damaged by an edge of an end portion of the metal member being mounted on the outer circumference of the shaft.

In order to avoid such a problem, the outer circumference of the shaft to which the metal member is attached is cut by an amount corresponding to the wall thickness of the metal member, and thus the outer diameter of the metal member may be coincided with the outer diameter of the shaft (uncut portion). However, since the diameter of the shaft of an endoscope used for diagnostic treatment of biliary ducts and pancreatic ducts is small, a cutting allowance cannot be sufficiently secured, and thus, when attempting to secure the cutting allowance, the diameter of a forceps channel or the like of the endoscope cannot be sufficiently secured.

Further, a fixing force between the outer circumference of the shaft made of resin and the inner circumference of the metal member made of metal is not sufficient. Accordingly, for example, during pulling operation of the operation wire, a positional shift may be caused as the metal member rotates about the shaft.

Furthermore, with the cylindrical metal member attached, a portion of the distal end portion of the shaft (portion to which the metal member is attached) cannot be warped, and thus smooth deflection operation cannot be performed.

The present invention has been made on the basis of the above-described circumstances.

An object of the present invention is to provide a medical device that is configured such that a distal end of an operation wire for performing distal end deflection operation can be securely fixed to a distal end of a shaft so that by reliably warping the entire distal end portion of the shaft, smooth deflection operation can be performed without body tissue and the like being damaged during body insertion or during pulling operation.

Solution to Problem (1) A medical device according to an aspect of the present invention is a medical device provided with a distal end deflection-operable shaft, the medical device including:

the shaft, in which at least one working lumen and at least one wire lumen are formed, the shaft being made of resin and including a distal end flexible portion;

a distal end tip that has, at least on a base end thereof, an outer diameter substantially equal to that of the shaft (for example, 80 to 120% of the outer diameter of the shaft) and in which a distal end working lumen in communication with the working lumen of the shaft and open at a distal end surface of the distal end tip is formed, the distal end tip being made of resin and disposed on a distal end side of the shaft;

an intermediate member made of metal or ceramic, disposed between the shaft and the distal end tip, and formed in a plate shape, preferably, a disk shape having an outer diameter substantially equal to that of the shaft (for example, 80 to 100% of the outer diameter of the shaft), the intermediate member including a main through-hole that is formed to secure a communication path with the working lumen of the shaft and the distal end working lumen of the distal end tip and surround the communication path, and a sub-through-hole that is formed to correspond to a position in which the wire lumen is formed; and an operation wire including a distal end large-diameter portion that is embedded in the distal end tip and has a diameter larger than a diameter of the sub-through-hole of the intermediate member, the operation wire passing through the sub-through-hole and extending in the wire lumen of the shaft and including a tail end that can be pulled. The shaft and the distal end tip are directly bonded on an inner side of the main through-hole of the intermediate member and on an outer side of the communication path.

According to the medical device configured as just described, the distal end of the operation wire is securely fixed to the distal end of the shaft by the intermediate member disposed between the shaft made of resin and the distal end tip made of resin. In other words, when the tail end of the operation wire is pulled, the distal end large-diameter portion of the distal end gets caught on the sub-through-hole of the intermediate member; therefore, the distal end of the operation wire can be restricted from moving in a base end direction. As a result, the distal end flexible portion of the shaft can be reliably warped. Note that the "outer diameter" of the intermediate member not formed in a disk shape is the "maximum outer diameter".

Further, since the intermediate member is formed in a plate shape having an outer diameter substantially equal to that of the shaft, the outer circumferential surfaces of the shaft, the intermediate member, and the distal end tip are flush with one another. Accordingly, the edge of the intermediate member is not exposed from between the shaft and the distal end tip, and body tissue and the like are not damaged by the edge of the intermediate member.

Furthermore, since the intermediate member is formed in a plate shape located on the distal end side of the shaft, the entire distal end flexible portion of the shaft is warped and smooth deflection operation can be performed.

In addition, the shaft and the distal end tip are directly bonded on the inner side of the main through-hole of the intermediate member and on the outer side of the communication path (the constituent resins of the shaft and the distal end tip are welded). Therefore, the intermediate member is also secured by the resin present on the inner side of the main through-hole, and a positional shift is not caused as the intermediate member rotates about the axis of the shaft.

Moreover, the shaft and the distal end tip are directly bonded on the inner side of the main through-hole of the intermediate member and on the outer side of the communication path (the constituent resins of the shaft and the distal end tip are welded). Thus, although the intermediate member made of metal or ceramic is interposed between the shaft and the distal end tip, the distal end tip can be firmly secured to the shaft, and the distal end tip does not fall off from the distal end of the shaft.

Further, the distal end large-diameter portion of the operation wire is embedded in the distal end tip, and thus the distal end of the operation wire opposed to the operation wire that is pulled does not move (extend out) in the distal end direction.

Furthermore, since the disk-shaped intermediate member is mounted differently from a case where a cylindrical metal member is mounted, it is not necessary to cut the outer circumference of the shaft (secure a cutting allowance). Therefore, even when the shaft has a small diameter, the diameter of the working lumen can be sufficiently secured.

(2) In the medical device according to an aspect of the present invention, it is preferable that a diameter of the communication path defined and formed by the constituent resin of the shaft and/or the distal end tip is substantially equal to diameters of the working lumen of the shaft and the distal end working lumen of the distal end tip (for example, the diameter of the working lumen and the diameter of the distal end working lumen are both 80 to 120% of the diameter of the communication path).

According to the medical device configured as just described, the diameter of the lumen including the communication path is substantially not changed from the base end of the shaft to the distal end of the distal end tip. Therefore, a tool that allows for insertion of the working lumen can be prevented from getting caught halfway.

(3) In the medical device according to an aspect of the present invention, a plurality of the working lumens are formed in the shaft, and accordingly, it is preferable that a plurality of distal end working lumens are also formed in the distal end tip.

(4) In the medical device of (3) described above, one main through-hole surrounding all of the communication paths is preferably formed in the intermediate member.

According to the medical device configured as just described, the area in which the shaft and the distal end tip are directly bonded can be sufficiently secured, and the bonding force between the shaft and the distal end tip can be further increased.

(5) In the medical device according to an aspect of the present invention, one working lumen is formed in the shaft, and accordingly, one distal end working lumen may also be formed in distal end tip.

(6) In the medical device according to an aspect of the present invention, the outer diameter of the intermediate member is preferably slightly smaller than an outer diameter of the shaft and the outer diameter of the distal end tip, and an outer circumference of the intermediate member is preferably covered by a resin coating such that a step between the shaft and the distal end tip due to the slightly smaller outer diameter of the intermediate member is eliminated.

According to the medical device configured as just described, the edge of the intermediate member can be prevented from being exposed even in a case where a slight positional shift in a radial direction of the intermediate member with respect to the shaft and the distal end tip is caused, for example, by repeated pulling operation.

(7) A medical device according to an aspect of the present invention that is used as an endoscope is a medical device provided with a distal end deflection-operable shaft, the medical device including:

the shaft, in which a camera channel, a water channel, and a forceps channel are formed as working lumens and in which four wire lumens are formed, the shaft being made of resin and including a distal end flexible portion;

a handle disposed on a base end side of the shaft and provided with a rotational operation portion;

a distal end tip in which a camera channel, a water channel, and a forceps channel are formed as distal end working lumens that are respectively in communication with the working lumens (the camera channel, the water channel, and the forceps channel) of the shaft and are open at a distal end surface of the distal end tip, the distal end tip being made of resin, disposed on a distal end side of the shaft, and having an outer diameter substantially equal to that of the shaft;

an intermediate member made of metal or ceramic, disposed between the shaft and the distal end tip, and formed in a plate shape, preferably, a disk shape having an outer diameter substantially equal to that of the shaft, the intermediate member including a main through-hole that is formed to ensure communication paths respectively with the working lumens (the camera channel, the water channel, and the forceps channel) of the shaft and the distal end working lumens (the camera channel, the water channel, and the forceps channel) of the distal end tip and surround all of the communication paths, and four sub-through-holes that are formed to correspond to positions in which the wire lumens are formed; and four operation wires including distal end large-diameter portions that are embedded in the distal end tip and have diameters larger than diameters of the sub-through-holes of the intermediate member, the operation wires respectively passing through the sub-through-holes and respectively extending in the wire lumens of the shaft, and including respective tail ends that are fixed to the rotational operation portion of the handle and thereby can be pulled. The shaft and the distal end tip are directly bonded on an inner side of the main through-hole of the intermediate member and on an outer side of each of the communication paths.

In this medical device, the "outer diameter" of the intermediate member not formed in a disk shape is the "maximum outer diameter".

(8) A medical device according to an aspect of the present invention, used as a steerable sheath is a medical device provided with a distal end deflection-operable shaft, the medical device including:

the shaft, in which one working lumen extending along a central axis of the distal end flexible portion and two wire lumens disposed opposed to each other with the working lumen interposed therebetween are formed, the shaft being made of resin and including a distal end flexible portion;

a handle disposed on a base end side of the shaft and provided with a rotational operation portion;

a distal end tip that has, at least on a base end thereof, an outer diameter substantially equal to that of the shaft and in which a distal end working lumen in communication with the working lumen of the shaft and open at a distal end surface of the distal end tip is formed, the distal end tip being made of resin and disposed on a distal end side of the shaft;

an intermediate member made of metal or ceramic, disposed between the shaft and the distal end tip, and formed in a plate shape, preferably, a disk shape having an outer diameter substantially equal to that of the shaft, the intermediate member including a main through-hole, preferably having a circular shape, that is formed to ensure a communication path with the working lumen of the shaft and the distal end working lumen of the distal end tip and surround the communication path, and two sub-through-holes that are formed to correspond to positions in which the wire lumens are formed; and two operation wires including distal end large-diameter portions that are embedded in the distal end tip and have diameters larger than diameters of the sub-through-holes of the intermediate member, the operation wires respectively passing through the sub-through-holes and respectively extending in the wire lumens of the shaft, and including respective tail ends that can be pulled by rotating the rotational operation portion of the handle. The shaft and the distal end tip are directly bonded on an inner side of the main through-hole of the intermediate member and on an outer side of the communication path.

In this medical device, the "outer diameter" of the intermediate member not formed in a disk shape is the "maximum outer diameter".

Advantageous Effects of Invention

According to the medical device of the present invention, the distal end of the operation wire for performing distal end deflection operation can be securely fixed to the distal end of the shaft so that by reliably warping the entire distal end portion of the shaft, smooth deflection operation can be performed without body tissue and the like being damaged during body insertion or during pulling operation.

Additionally, although the intermediate member made of metal or ceramic is interposed between the shaft made of resin and the distal end tip made of resin, the distal end tip can be firmly secured to the shaft, and the distal end tip does not fall off from the distal end of the shaft.

6

Figure 1:
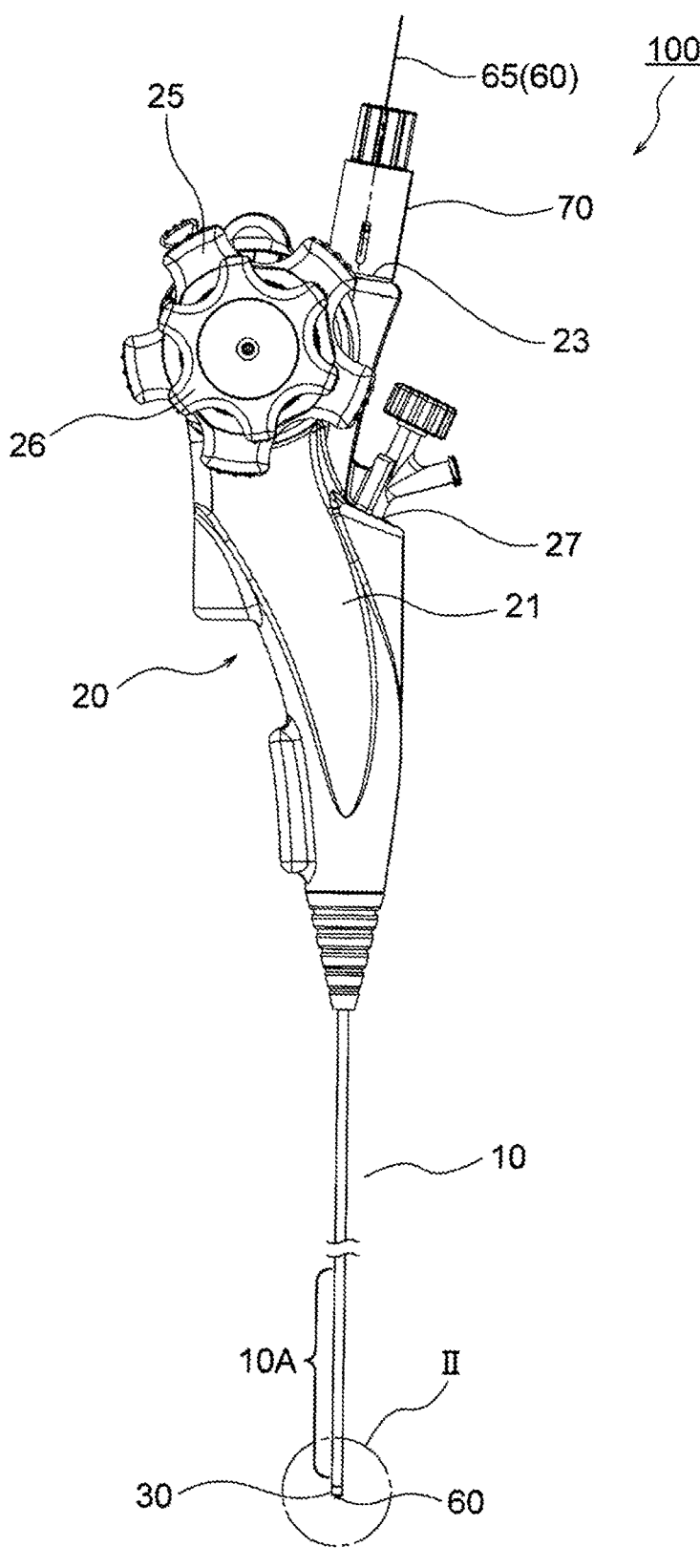
FIG. 1 is an explanatory diagram illustrating the outer appearance of an endoscope that is a first embodiment of a medical device of the present invention.
Figure 2:
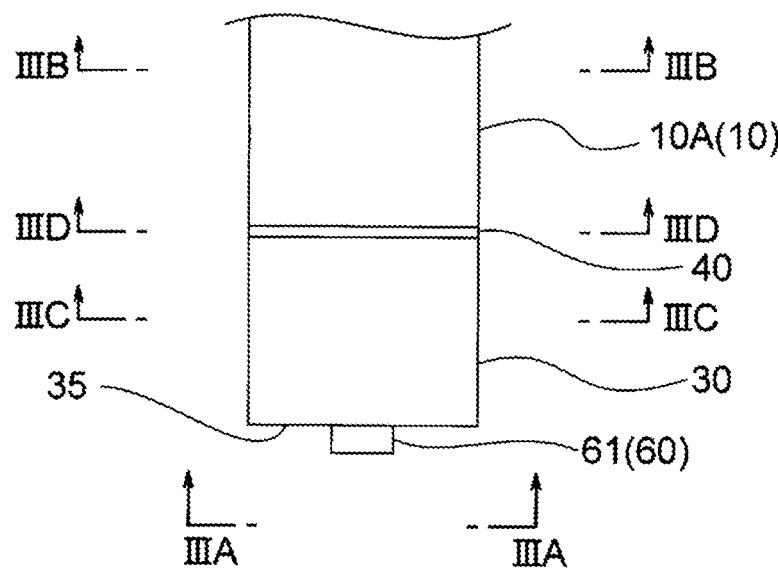

FIG. 2 is a partially enlarged view (detail view of portion II) illustrating a distal end portion of the endoscope illustrated in FIG. 1.

Figure 3A:
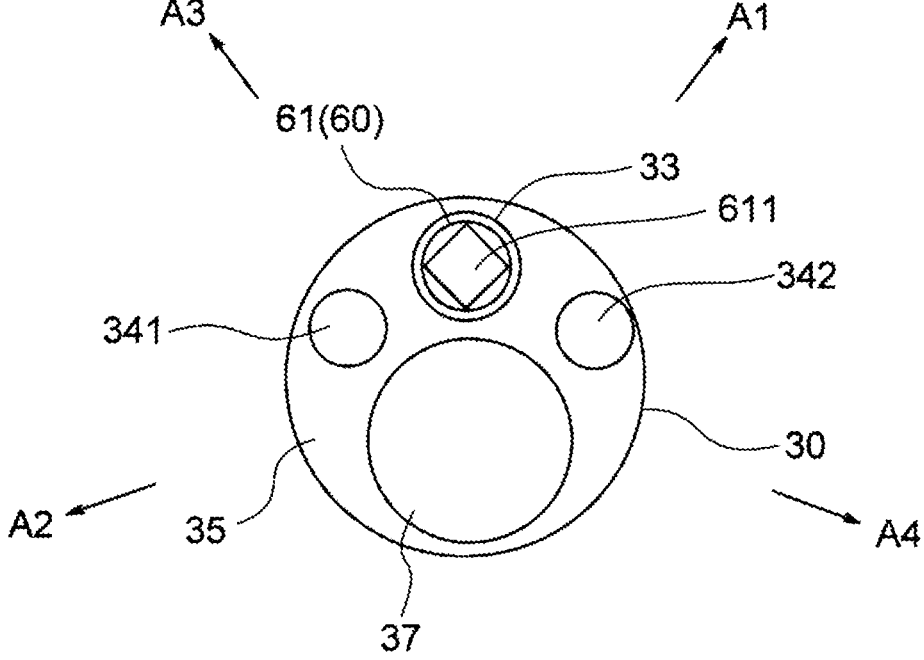

FIG. 3A is a view taken in the direction of the arrows IIIA-IIIA in FIG. 2.

Figure 3B:
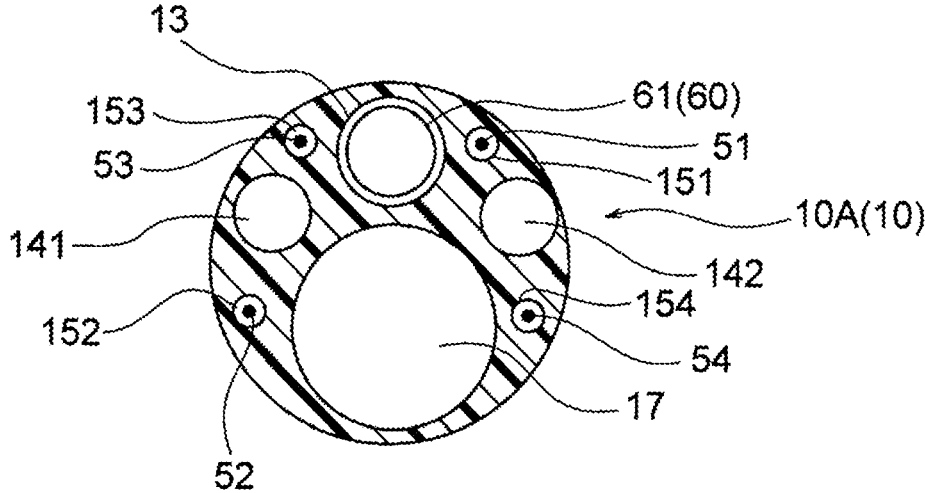

FIG. 3B is a cross-sectional view taken along the line IIIB-IIIB in FIG. 2 (a cross-sectional view of a shaft).

Figure 3C:
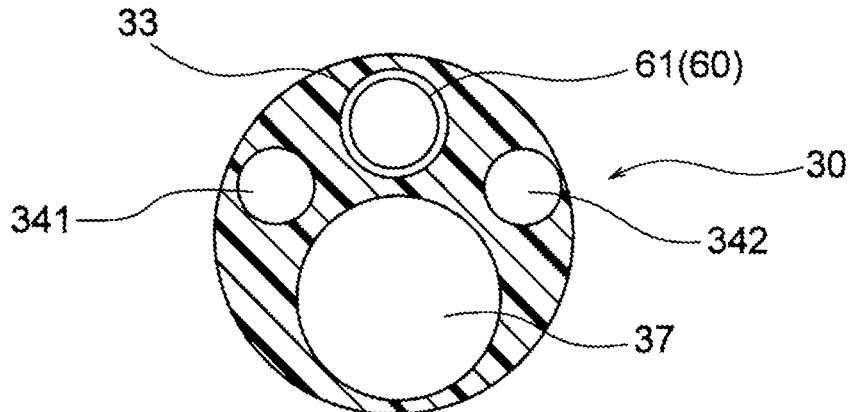

FIG. 3C is a cross-sectional view taken along the line IIIC-IIIC in FIG. 2 (a cross-sectional view of a distal end tip).

Figure 3D:
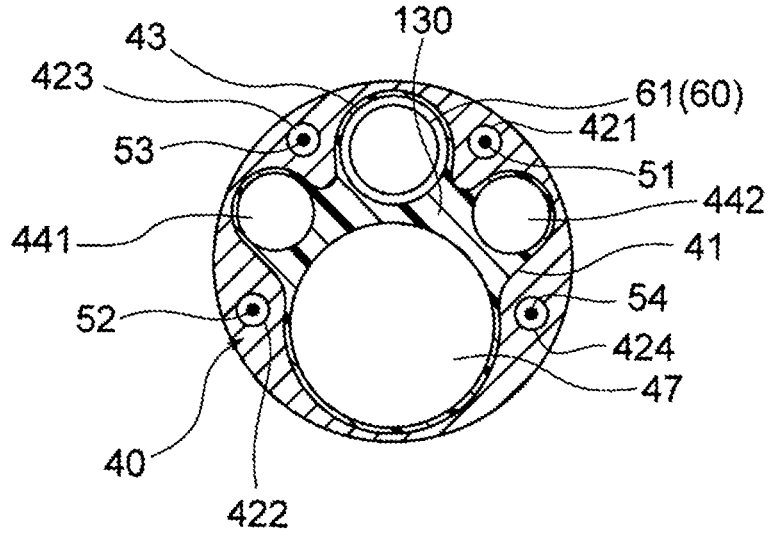

FIG. 3D is a cross-sectional view taken along the IIID-IIID in FIG. 2 (a cross-sectional view of an intermediate member).

Figure 4A:
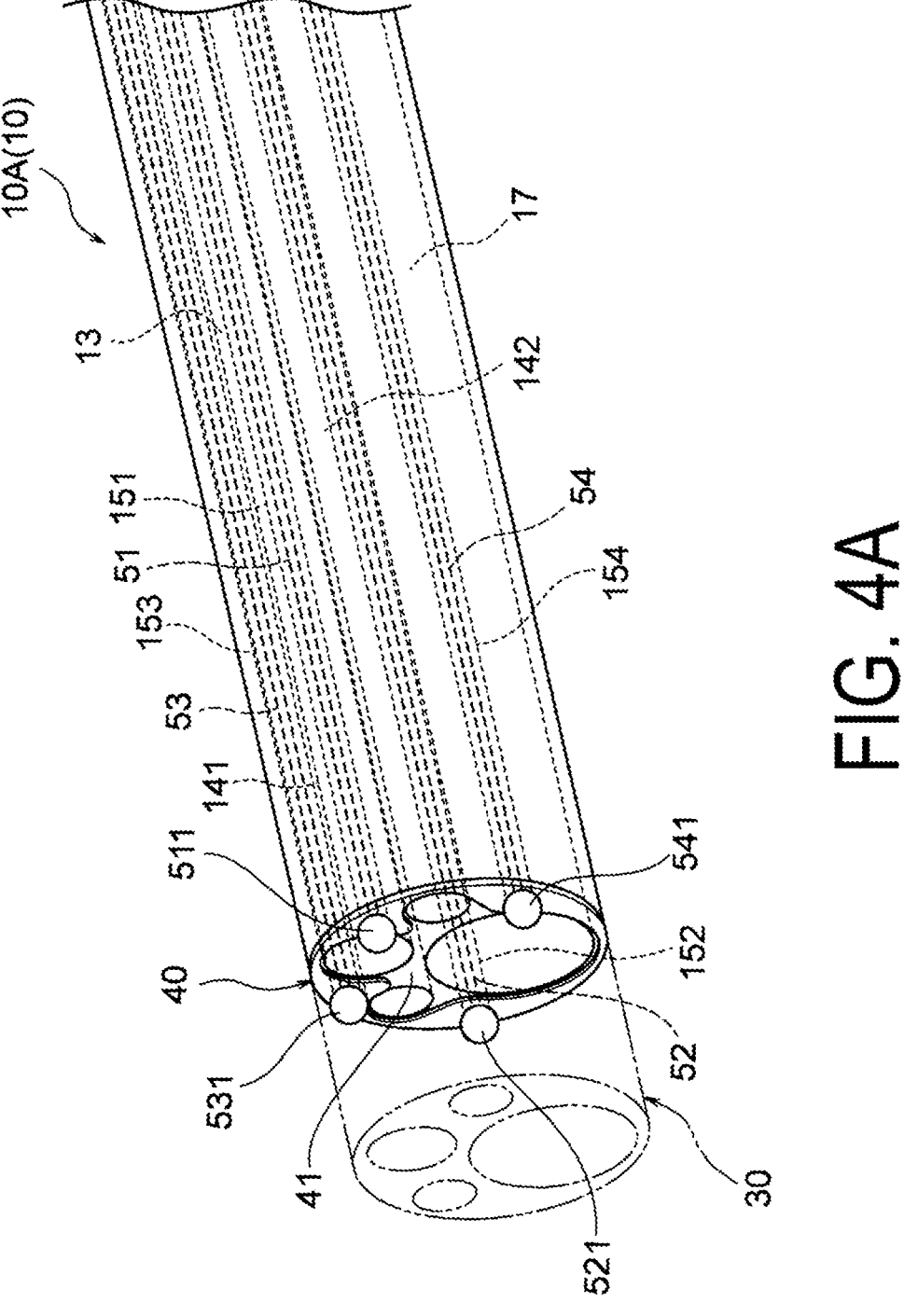

FIG. 4A is a perspective view illustrating a distal end portion of the endoscope illustrated in FIG. 1 (a camera is not illustrated).

Figure 4B:
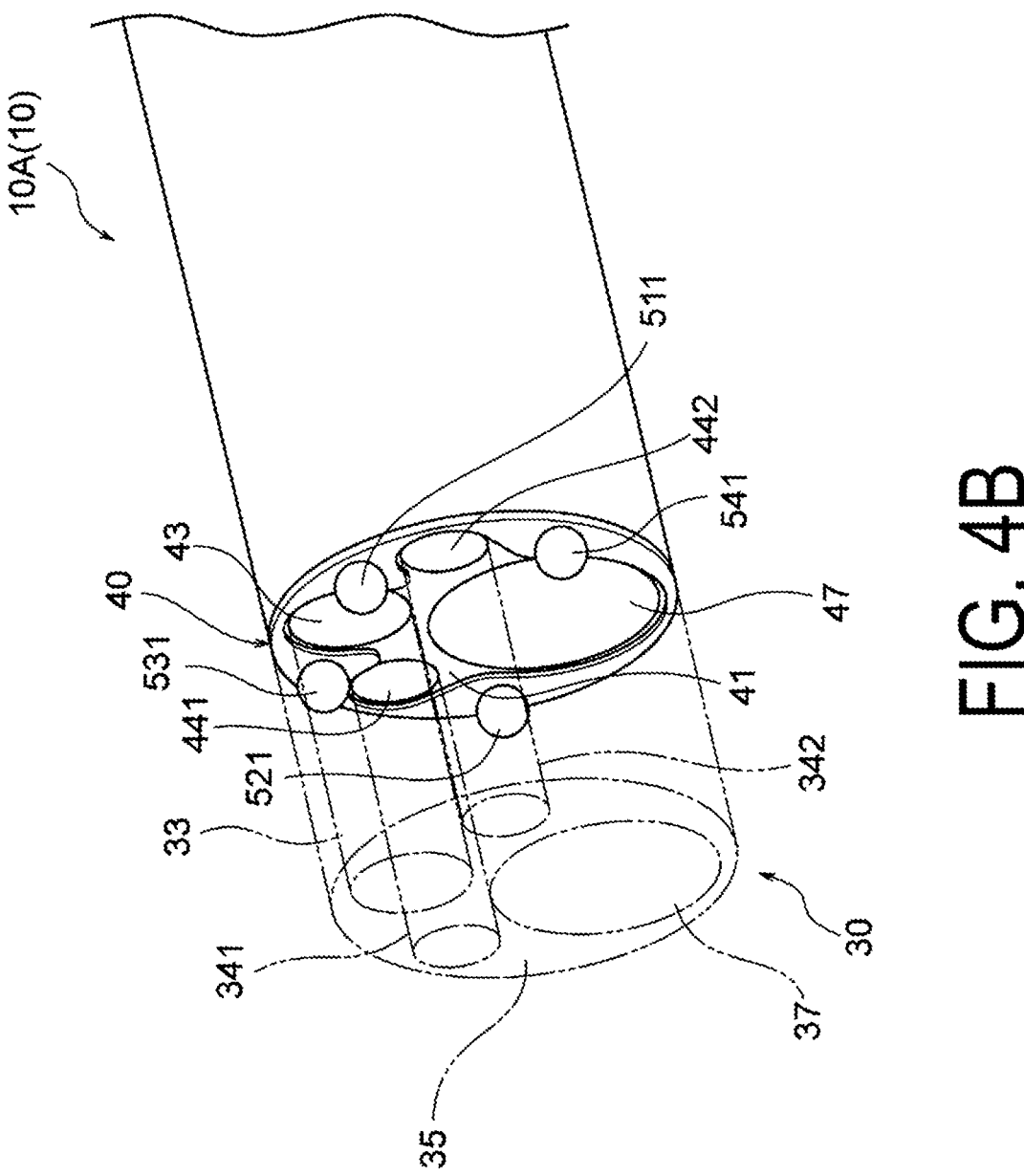

FIG. 4B is a perspective view illustrating the distal end portion of the endoscope illustrated in FIG. 1 (the camera is not illustrated).

Figure 5A:
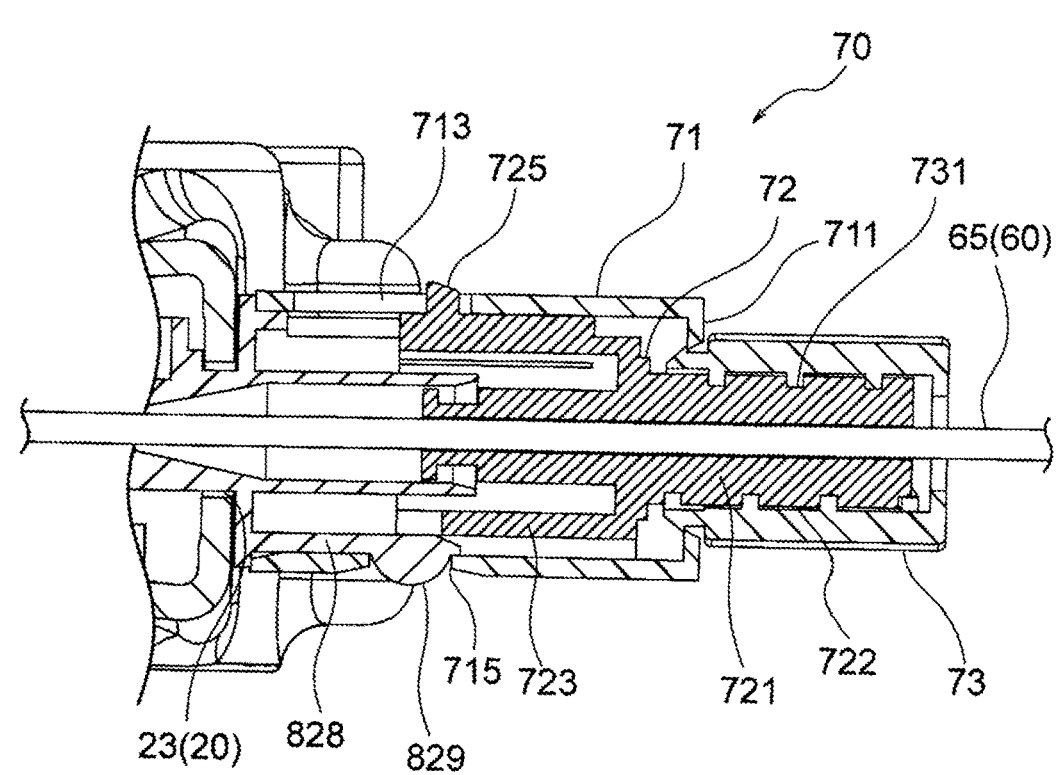

FIG. 5A is a cross-sectional view illustrating a state where a slide member of a camera connector constituting the endoscope illustrated in FIG. 1 is at a base end position.

Figure 5B:
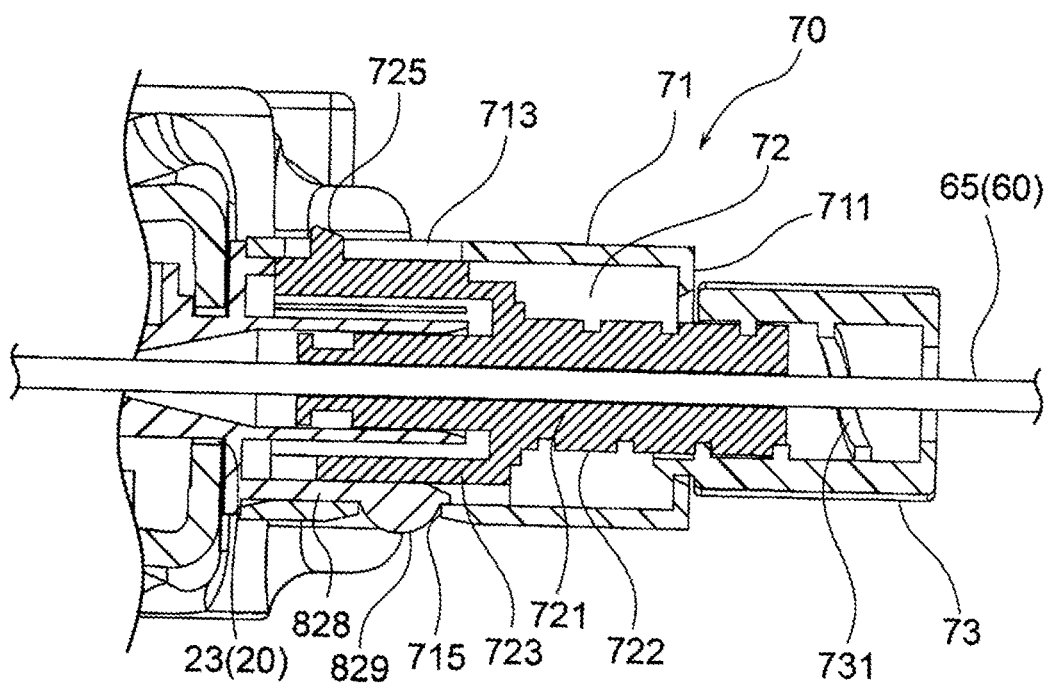

FIG. 5B is a cross-sectional view illustrating a state where the slide member of the camera connector constituting the endoscope illustrated in FIG. 1 is at a distal end position.

Figure 6A:
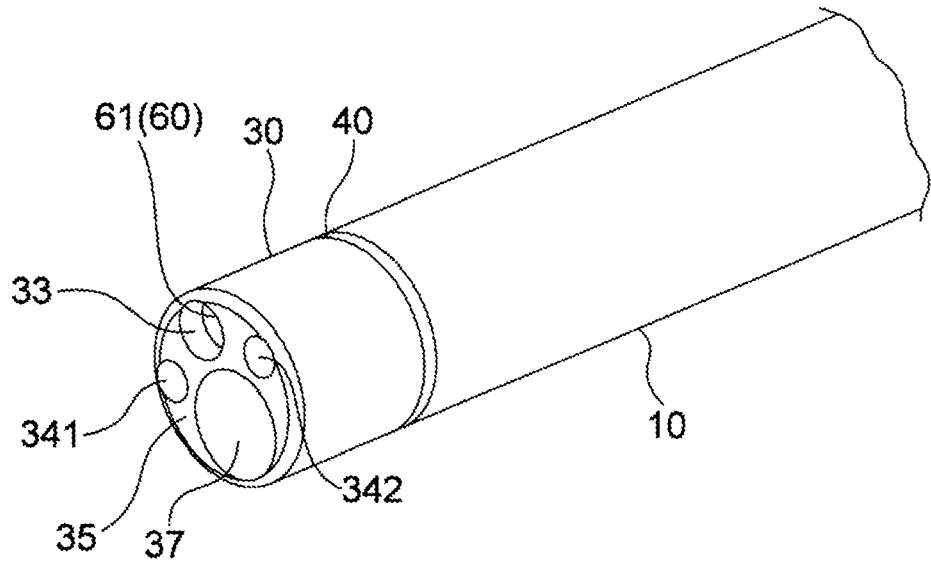

FIG. 6A is a perspective view illustrating a state where a distal end of the camera constituting the endoscope illustrated in FIG. 1 is at a first position on a base end side of a distal end surface of the distal end tip.

Figure 6B:
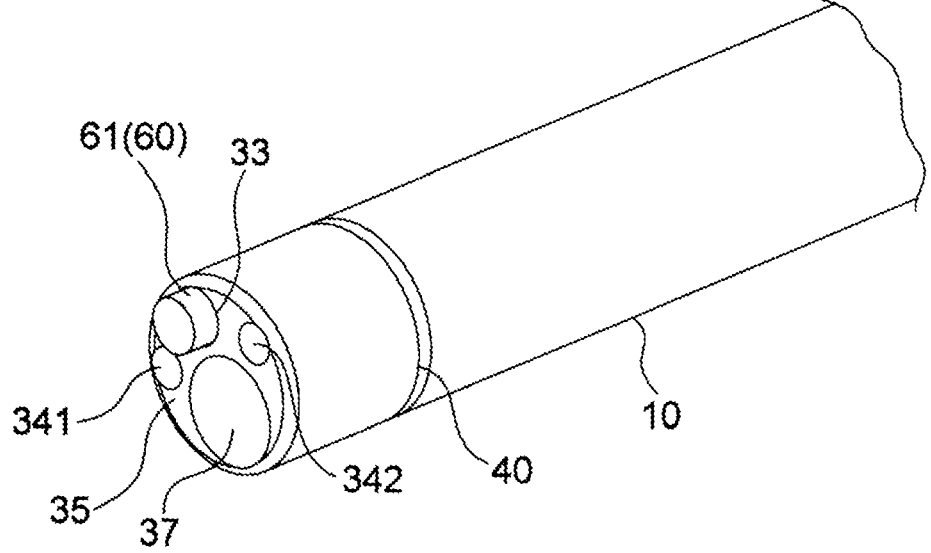

FIG. 6B is a perspective view illustrating a state where the distal end of the camera constituting the endoscope illustrated in FIG. 1 is at a second position on a distal end side of the distal end surface of the distal end tip.

Figure 7:
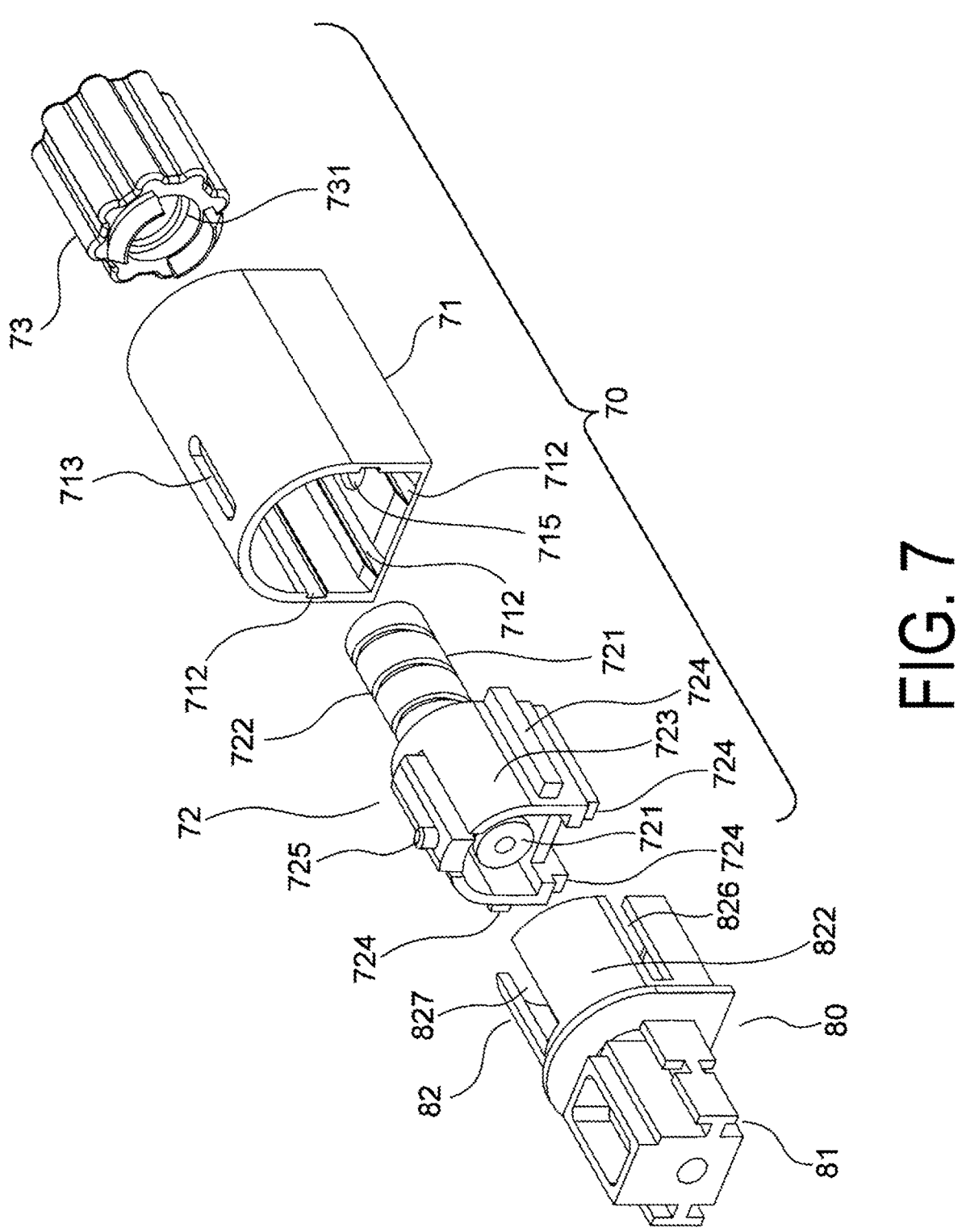

FIG. 7 is an exploded perspective view illustrating constituent members of a camera position adjustment mechanism and a connector mounting restriction mechanism in the endoscope illustrated in FIG. 1.

Figure 8:
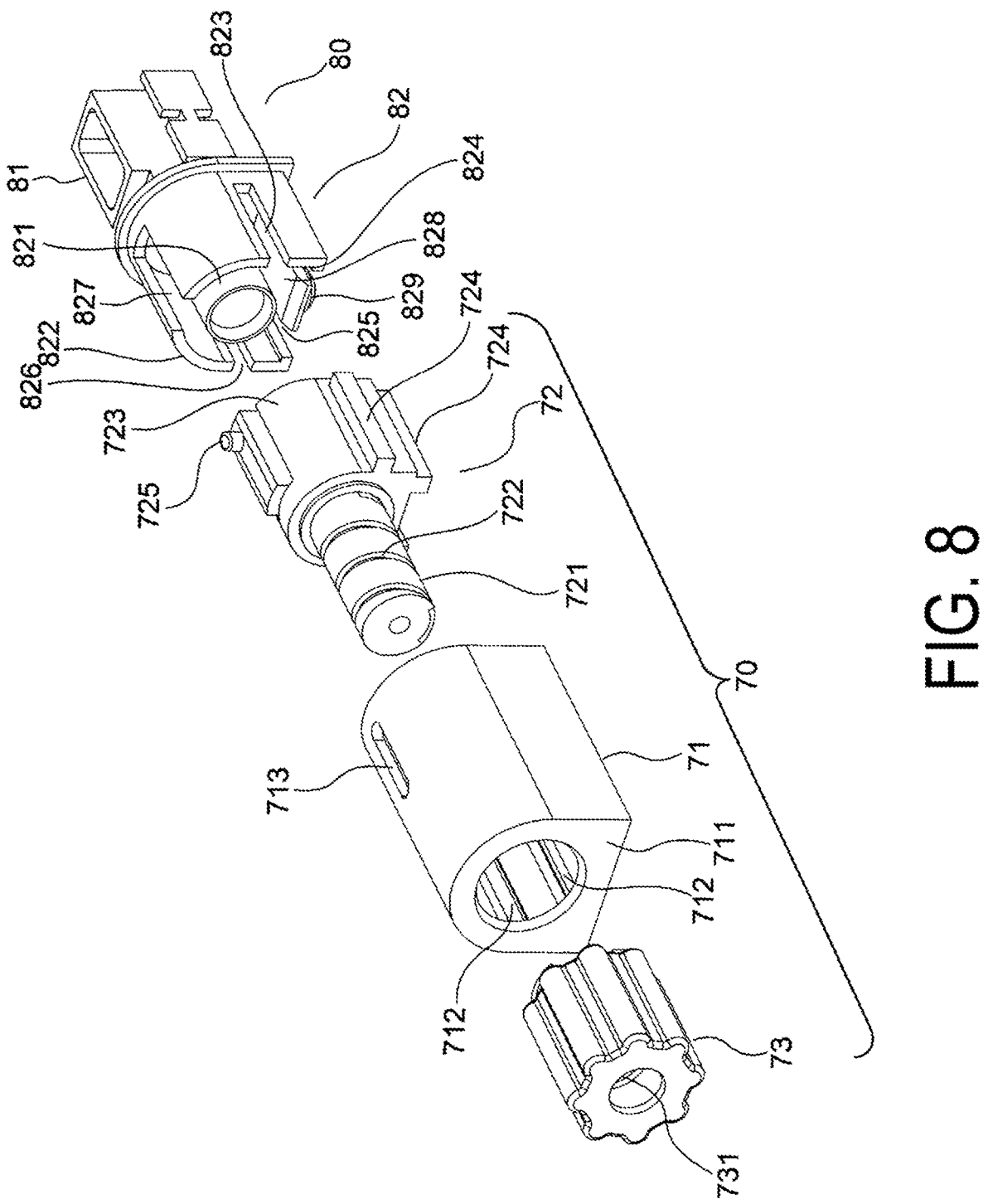

FIG. 8 is an exploded perspective view illustrating constituent members of the camera position adjustment mechanism and the connector mounting restriction mechanism in the endoscope illustrated in FIG. 1.

Figure 9A:
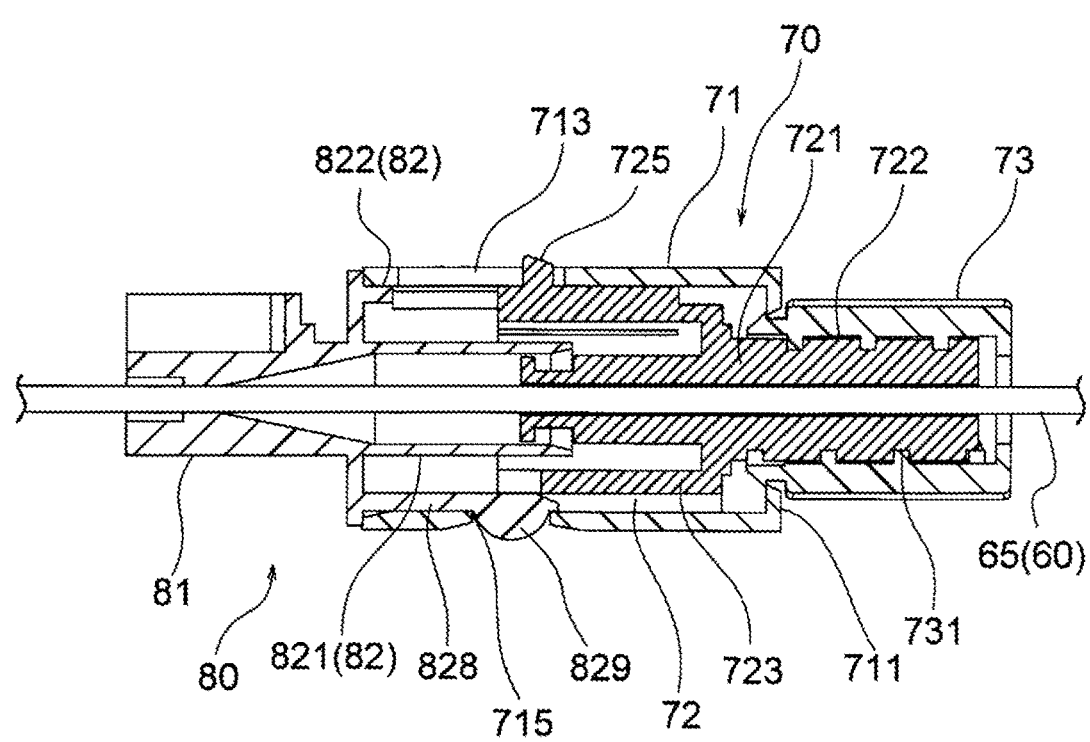

FIG. 9A is a cross-sectional view illustrating a state where a port-side connector and the camera connector that constitute the endoscope illustrated in FIG. 1 are connected.

Figure 9B:
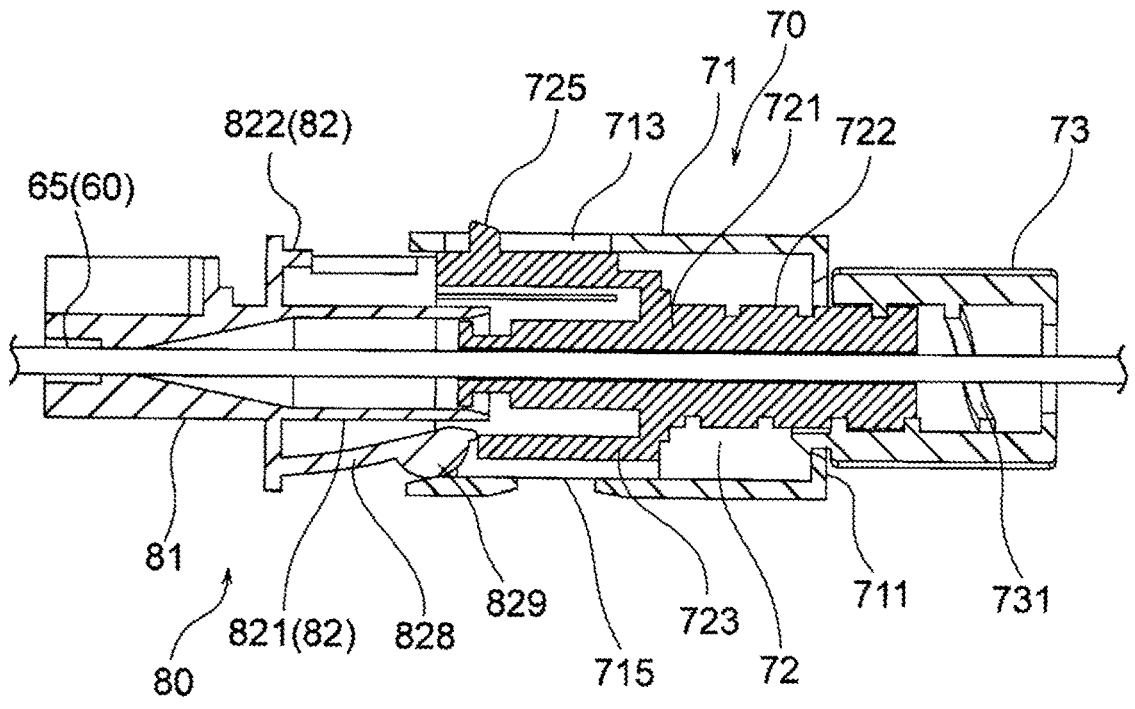

FIG. 9B is a cross-sectional view illustrating a state where the connection between the port-side connector and the camera connector that constitute the endoscope illustrated in FIG. 1 is restricted.

Figure 10:
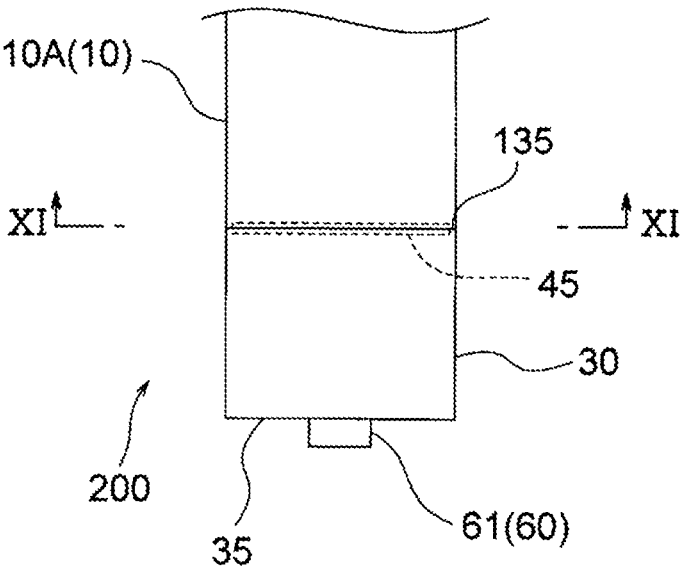

FIG. 10 is an explanatory diagram illustrating the distal end portion of the endoscope that is a second embodiment of the medical device of the present invention.

Figure 11:
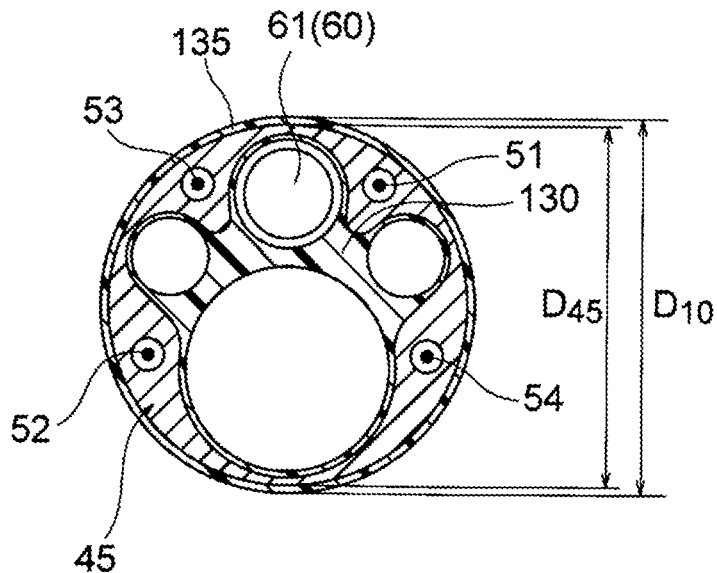

FIG. 11 is a cross-sectional view taken along the line XI-XI in FIG. 10.

Figure 12:
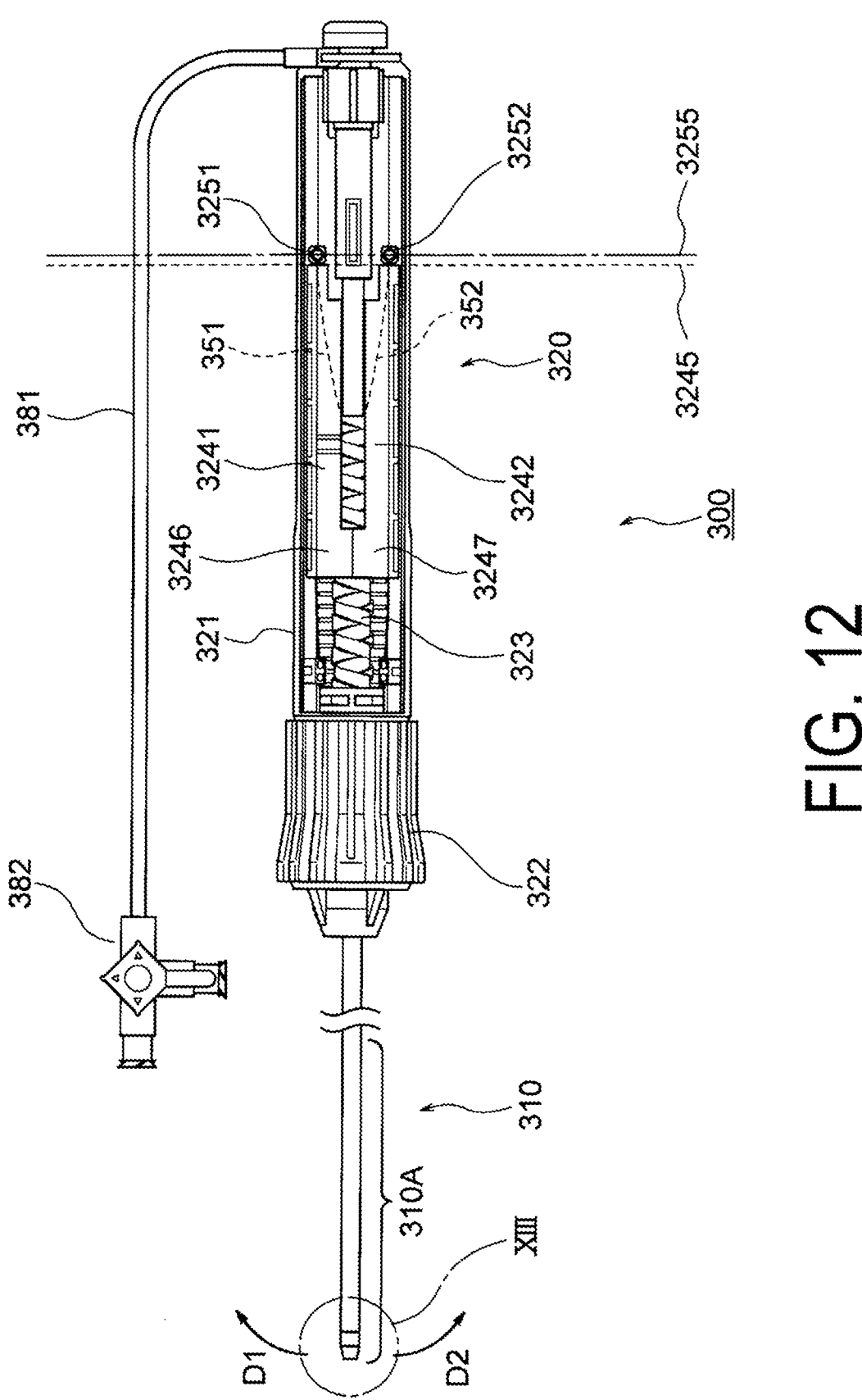

FIG. 12 is a plan view illustrating the interior of a handle when a distal end flexible portion of a shaft is in a linear state in a steerable sheath that is a third embodiment of the medical device of the present invention.

Figure 13:
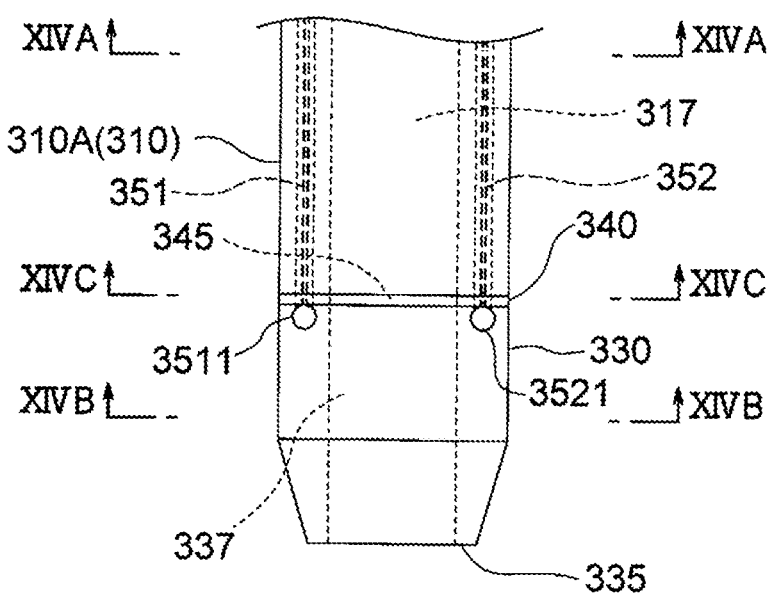

FIG. 13 is a partially enlarged view (detail view of portion XIII) of a distal end portion of the steerable sheath illustrated in FIG. 12.

Figure 14A:
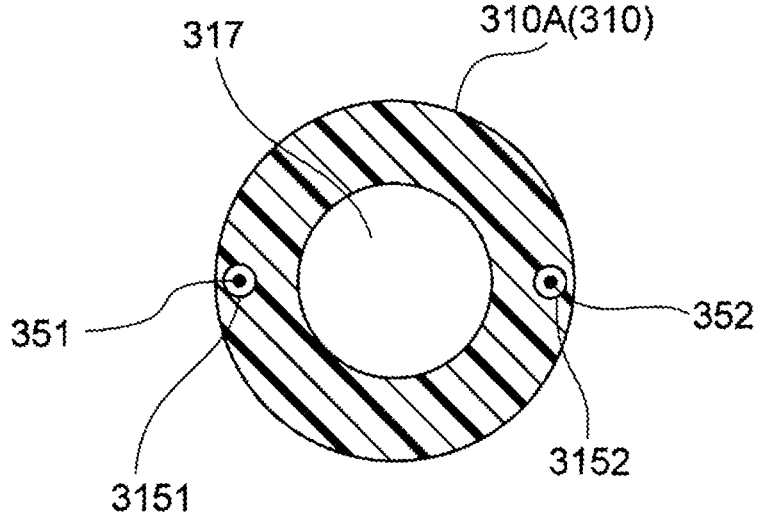

FIG. 14A is a cross-sectional view taken along the line XIVA-XIVA in FIG. 13 (a cross-sectional view of the shaft).

Figure 14B:
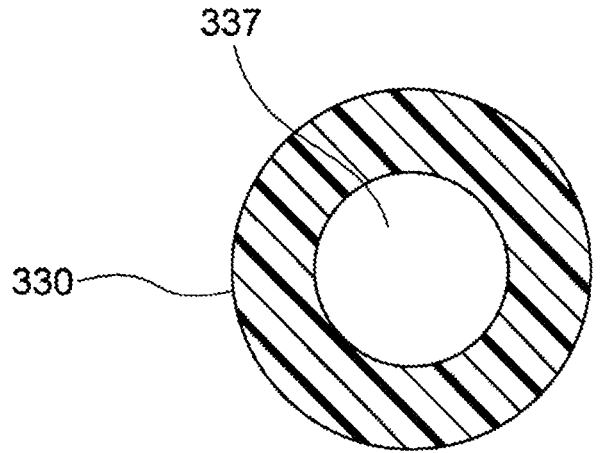

FIG. 14B is a cross-sectional view taken along the XIVB-XIVB in FIG. 13 (a cross-sectional view of a distal end tip).

Figure 14C:
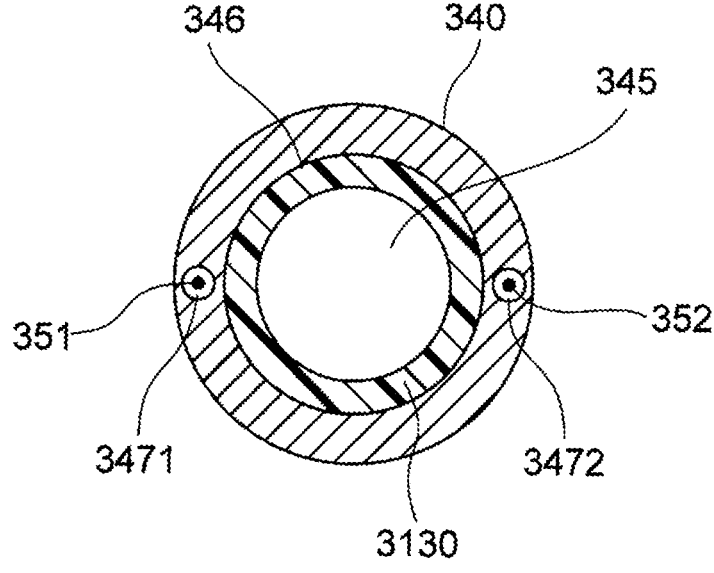

FIG. 14C is a cross-sectional view taken along the XIVC-XIVC in FIG. 13 (a cross-sectional view of an intermediate member).

Figure 15:
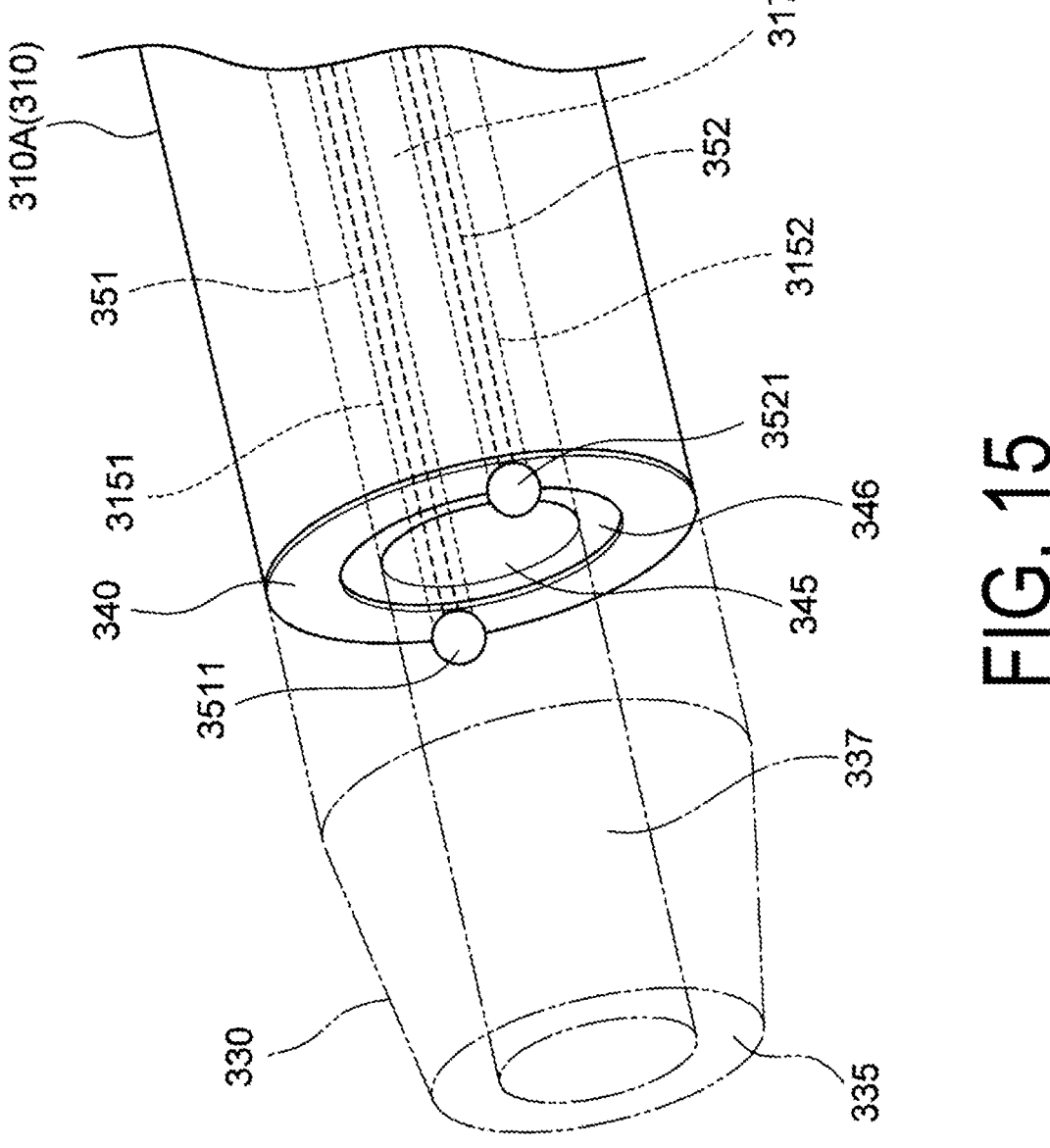

FIG. 15 is a perspective view illustrating the distal end portion of the steerable sheath illustrated in FIG. 12.

Figure 16:
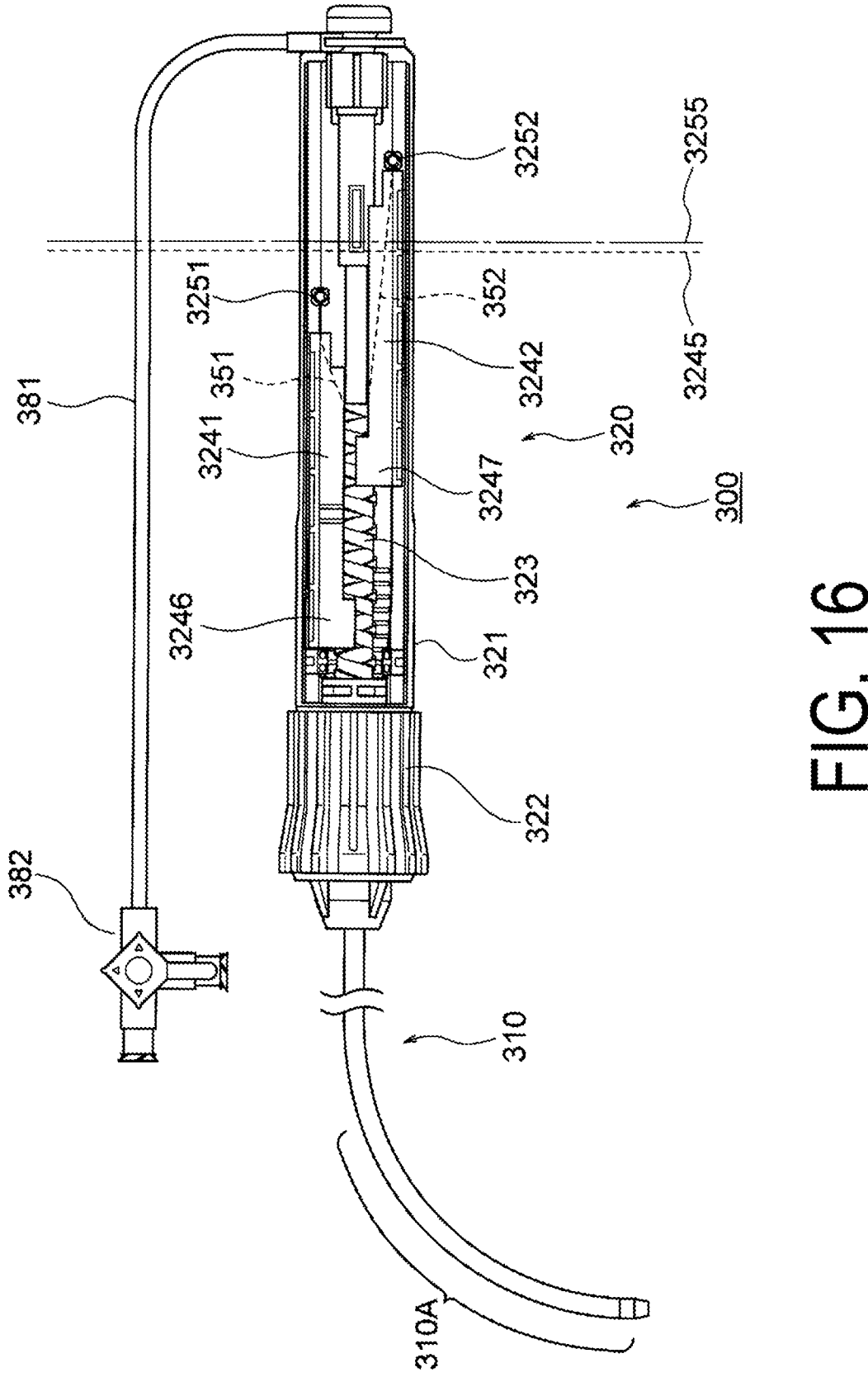

FIG. 16 is a plan view illustrating the interior of the handle when the distal end flexible portion of the shaft is warped in the steerable sheath illustrated in FIG. 12.

DESCRIPTION OF EMBODIMENTS

First Embodiment

An endoscope according to a first embodiment of a medical device of the present invention will be described.

An endoscope 100 of this embodiment illustrated in FIGS. 1 to 9 (FIGS. 9A and 9B) is used for diagnostic treatment of diseases in biliary ducts or pancreatic ducts.

The endoscope 100 includes: a shaft 10 in which a camera channel 13, two water channels 141, 142, and a forceps channel 17 are formed as working lumens and in which four wire lumens 151, 152, 153, 154 are formed, the shaft 10 being made of resin and including a distal end flexible portion 10A; a handle 20 disposed on a base end side of the shaft 10 and provided with a rotational operation portion (an operation knob 25 and an operation knob 26); a distal end tip 30 in which a camera channel 33, water channels 341, 342, and a forceps channel 37 are formed as distal end working lumens that are respectively in communication with the working lumens (the camera channel 13, the water channels 141, 142, and the forceps channel 17) of the shaft 10 and are open at a distal end surface 35 of the distal end tip, the distal end tip 30 being made of resin, disposed on a distal end side of the shaft 10, and having an outer diameter equal to that of the shaft 10; an intermediate member 40 made of metal, disposed between the shaft 10 and the distal end tip 30, and formed in a disk shape having an outer diameter equal to that of the shaft 10, the intermediate member 40 including a main through-hole 41 that is formed to ensure communication paths 43, 441, 442, 47 respectively with the working lumens (the camera channel 13, the water channels 141, 142, and the forceps channel 17) of the shaft 10 and the distal end working lumens (the camera channel 33, the water channels 341, 342, and the forceps channel 37) of the distal end tip 30 and surround all of the communication paths 43, 441, 442, 47, and four sub-through-holes 421, 422, 423, 424 that are formed to correspond to the positions in which the wire lumens 151, 152, 153, 154 of the shaft 10 are formed; four operation wires 51, 52, 53, 54 including distal end large-diameter portions 511, 521, 531, 541 that are embedded in the distal end tip 30 and have diameters larger than diameters of the sub-through-holes 421, 422, 423, 424 of the intermediate member 40, the operation wires 51, 52, 53, 54 respectively passing through the sub-through-holes 421, 422, 423, 424 and respectively extending in the wire lumens 151, 152, 153, 154 of the shaft 10, and including respective tail ends that are fixed to the rotational operation portion (the operation knob 25 or the operation knob 26) of the handle 20 and thereby can be pulled; and a camera 60 arranged in the camera channel 13 of the shaft 10 and the camera channel 33 of the distal end tip 30 and separable from the shaft 10 and the handle 20. The shaft 10 and the distal end tip 30 are directly bonded on the inner side of the main through-hole 41 of the intermediate member 40 and on the outer side of each of the communication paths 43, 441, 442, 47 (the constituent resins of the shaft and the distal end tip are welded).

The endoscope 100 includes the shaft 10 to be inserted into the body, the handle 20 disposed on the base end side of the shaft 10, the distal end tip 30 disposed on the distal end side of the shaft 10, the intermediate member 40 disposed between the shaft 10 and the distal end tip 30, the operation wires 51, 52, 53, 54, and the camera 60.

As illustrated in FIGS. 3B and 4A, the camera channel 13, the water channels 141, 142, and the forceps channel 17 are formed as working lumens in the shaft 10 constituting the endoscope 100.

Also, the wire lumens 151, 152, 153, 154 that are insertion paths for the operation wires 51, 52, 53, 54, are formed in the shaft 10.

The length (effective length) of the shaft 10 is preferably 200 to 4800 mm, and is 1900 mm as one preferred example.

The shaft 10 includes the distal end flexible portion 10A.

Here, the "distal end flexible portion" refers to a distal end portion of the shaft, which can be warped (bent) by pulling the tail end of the operation wire.

The length of the distal end flexible portion 10A is preferably 5 to 200 mm, and is 20 mm as one preferred example.

The outer diameter of the shaft 10 is preferably 1.1 to 13 mm, and is 3.6 mm as one preferred example.

The diameter of the camera channel 13 is preferably 0.6 to 4.0 mm, and is 1.1 mm as one preferred example.

The diameter of the water channels 141, 142 is preferably 0.2 to 3.0 mm, and is 0.7 mm as one preferred example.

The diameter of the forceps channel 17 is preferably 0.3 to 4.5 mm, and is 2.0 mm as one preferred example. The diameter of the forceps channel 17 is 2.0 mm, and thus a general-purpose forceps (1.8 mm diameter) can be used.

The shaft 10 is made of resin.

Examples of the resin material forming the shaft 10 can include nylon resin, polyether block amide (PEBAX) resin, polyurethane resin, polyolefin resin, and the like, and of these resins, PEBAX resin and polyurethane resin are preferable.

The hardness (Shore D hardness) of the constituent resin of the shaft 10 is preferably 90 D or less, and when one preferred example is given, the hardness of the resin forming the distal end flexible portion 10A is 25 D, and the hardness of the resin forming a portion other than the distal end flexible portion 10A is 30 D.

The handle 20 is disposed on the base end side of the shaft 10.

The handle 20 constituting the endoscope 100 includes a grip 21 and the two operation knobs 25, 26 as a rotational operation portion.

The handle 20 is provided with a camera channel port 23 in communication with the camera channel 13 and a forceps channel port 27 in communication with the forceps channel 17.

The distal end tip 30 is disposed on the distal end side of the shaft 10.

As illustrated in FIGS. 3A, 3C, and 4B, the camera channel 33, the water channels 341, 342, and the forceps channel 37 are formed as distal end working lumens in the distal end tip 30 constituting the endoscope 100.

Each of the distal end working lumens of the distal end tip 30 is in communication with each of the working lumens of shaft 10 via the communication path.

The camera channel 33 is in communication via the communication path 43 with the camera channel 13 of the shaft 10. The diameter of the camera channel 33 is equal to the diameter of the camera channel 13 in communication with the camera channel 33.

The water channels 341, 342 are respectively in communication with the water channels 141, 142 of the shaft 10 via the communication paths 441, 442. The diameter of the water channels 341, 342 is equal to the diameter of the water channels 141, 142 in communication with the water channels 341, 342.

The forceps channel 37 is in communication via the communication path 47 with the forceps channel 17 of shaft 10. The diameter of the forceps channel 37 is equal to the diameter of the forceps channel 17 in communication with the forceps channel 37.

The length of the distal end tip 30 is preferably 1 to 30 mm, and is 3 mm as one preferred example.

The outer diameter of the distal end tip 30 is equal to the outer diameter of the shaft 10.

The distal end tip 30 is made of resin.

Examples of the resin material forming the distal end tip 30 can include resins similar to those illustrated as the resins forming the shaft 10, and out of the resins, PEBAX resin and polyurethane resin are preferable.

The distal end tip 30 is made of a resin material having low hardness so as not to damage body tissue. The hardness (Shore D hardness) of the constituent resin of the distal end tip 30 is preferably 72 D or less, and is 25 D as one preferred example.

The intermediate member 40 formed in a disk shape is disposed between the shaft 10 and the distal end tip 30.

The intermediate member 40 constituting the endoscope 100 is a member for fixing a distal end of each of the operation wires 51, 52, 53, 54 to a distal end of the shaft 10 (for preventing removal of the tail end during pulling operation).

As illustrated in FIGS. 3D and 4B, one main through-hole 41 that surrounds all of the communication paths 43, the communication paths 441, 442, and the communication path 47 is formed in the intermediate member 40.

Here, the communication path 43 is a path (camera channel) defined and formed by a constituent resin 130 of the shaft 10 and/or the distal end tip 30 in order to allow the camera channel 13 of the shaft 10 to communicate with the camera channel 33 of the distal end tip 30. The diameter of the communication path 43 is equal to the diameters of the camera channel 13 and the camera channel 33.

The communication paths 441, 442 are paths (water channels) defined and formed by the constituent resin 130 of the shaft 10 and/or the distal end tip 30 in order to allow the water channels 141, 142 of the shaft 10 to respectively communicate with the water channels 341, 342 of the distal end tip 30. The diameter of the communication paths 441, 442 is identical to the diameters of the water channels 141, 142 and the water channels 341, 342.

The communication path 47 is a path (forceps channel) defined and formed by the constituent resin 130 of the shaft 10 and/or the distal end tip 30 to allow the forceps channel 17 of the shaft 10 to communicate with the forceps channel 37 of the distal end tip 30. The diameter of the communication path 47 is equal to the diameters of the forceps channel 17 and the forceps channel 37.

As illustrated in FIG. 3D, four sub-through-holes 421, 422, 423, 424 are formed in the intermediate member 40 to correspond to the positions in which the wire lumens 151, 152, 153, 154 of the shaft 10 are formed. The sub-through-holes 421, 422, 423, 424 are insertion paths for the operation wires 51, 52, 53, 54.

The sub-through-holes 421, 422, 423, 424 are circular holes, and the diameter of each of the sub-through-holes is larger than the diameter of the operation wires 51, 52, 53, 54 and is adjusted to be smaller than the diameter of the distal end large-diameter portions 511, 521, 531, 541 to restrict insertion thereof.

The diameter of the sub-through-hole is preferably 0.13 to 2.5 mm, and is 0.35 mm as one preferred example.

The thickness of the intermediate member 40 is preferably 0.05 to 3 mm, and is 0.15 mm as one preferred example.

When the thickness of the intermediate member 40 is excessively small, the intermediate member 40 may be damaged when receiving a mechanical shock associated with pulling of the operation wires 51, 52, 53, 54.

On the other hand, when the thickness is excessively large, the intermediate member 40 itself is less likely to warp, and thus the distal end flexible portion 10A may be difficult to warp.

The outer diameter of the intermediate member 40 is equal to the outer diameters of the shaft 10 and the distal end tip 30, and thus the outer circumferential surface of the shaft 10, the outer circumferential surface of the intermediate member 40, and the outer circumferential surface of the distal end tip 30 are flush with one another. Accordingly, the intermediate member 40 does not protrude from between the shaft 10 and the distal end tip 30 and the edge thereof is not exposed, and thus body tissue and the like are not damaged by such an edge.

The intermediate member 40 is made of metal or ceramic, and is preferably made of metal.

Example of the metal material forming the intermediate member 40 can include stainless copper, platinum, gold, copper, nickel, titanium, tantalum, and the like, and of the metals, stainless copper is preferable.

In the endoscope 100 of the present embodiment, the shaft 10 and the distal end tip 30 are directly bonded in a region on the inner side of the main through-hole 41 of the intermediate member 40 and on the outer side of each of the communication paths 43, 441, 442, 47 (a region surrounded by the main through-hole 41 excluding the communication paths)(the constituent resins of the shaft and the distal end tip are welded). As a result, the intermediate member 40 is also secured by the resin present on the inner side of the main through-hole 41, and the intermediate member 40 is firmly secured to the shaft 10 and the distal end tip 30.

Also, the shaft 10 and distal end tip 30 are directly bonded though partially bonded, and thus the fixing strength of the distal end tip 30 with respect to the shaft 10 is also sufficiently increased.

Here, the area of the region in which the constitution resin of the shaft 10 and the distal end tip 30 are directly bonded is (S) and the cross-sectional area of the shaft 10 is ($S_0$), the value of (S)/($S_0$) is preferably 0.1 or greater, and is more preferably 0.3 to 0.6.

As illustrated in FIGS. 3B and 4A, the operation wires 51, 52, 53, 54 extend respectively in the wire lumens 151, 152, 153, 154 of the shaft 10.

As illustrated in FIGS. 4A and 4B, the distal ends of the operation wires 51, 52, 53, 54 are respectively the distal end large-diameter portions 511, 521, 531, 541.

The distal end large-diameter portions 511, 521, 531, 541 are spherical or partially spherical shapes having a diameter larger than the diameter of the sub-through-holes 421, 422, 423, 424 of the intermediate member 40, and cannot pass through the sub-through-holes 421, 422, 423, 424.

The diameter of the distal end large-diameter portions 511, 521, 531, 541 is preferably 0.2 to 3.5 mm, and is 0.4 mm as one preferred example.

The diameter of the operation wires 51, 52, 53, 54 (a portion other than the distal end large-diameter portion) is preferably 0.1 to 2.0 mm, and is 0.25 mm as one preferred example.

The operation wires 51, 52 are held in a state where each of the distal end large-diameter portions 511, 521 is embedded in the distal end tip 30, and portions of the wires, which are located on the base end side from the distal end large-diameter portions 511, 521 pass through the sub-through-holes 421, 422 of the intermediate member 40 and extend in the wire lumens 151, 152 of the shaft 10. Each of the base ends of the operation wires 51, 52 is fixed to the operation knob 25 of the handle 20.

By rotating the operation knob 25 in one direction and pulling the base end of the operation wire 51, the operation wire 51 moves the wire lumen 151 in a base end direction. At this time, the distal end large-diameter portion 511 gets caught on the sub-through-hole 421 of the intermediate member 40 to be restrict from moving in the base end direction. Therefore, the distal end flexible portion 10A of the shaft 10 warps in the direction indicated by arrow A1 of FIG. 3A, and the distal end of the endoscope 100 (the distal end tip 30) deflects in the same direction.

By rotating the operation knob 25 in the other direction and pulling the base end of the operation wire 52, the operation wire 52 moves the wire lumen 152 in the base end direction. At this time, the distal end large-diameter portion 521 gets caught on the sub-through-hole 422 of the intermediate member 40 to be restrict from moving in the base end direction. Therefore, the distal end flexible portion 10A of the shaft 10 warps in the direction indicated by arrow A2 of FIG. 3A, and the distal end of the endoscope 100 (the distal end tip 30) deflects in the same direction.

The operation wires 53, 54 are held in a state where each of the distal end large-diameter portions 531, 541 is embedded in the distal end tip 30, and portions of the wires, which are located on the base end side from the distal end large-diameter portions 531, 541 pass through the sub-through-holes 423, 424 of the intermediate member 40 and extend in the wire lumens 153, 154 of the shaft 10. Each of the base ends of the operation wires 53, 54 is fixed to the operation knob 26 of the handle 20.

By rotating the operation knob 26 in one direction and pulling the base end of the operation wire 53, the operation wire 53 moves the wire lumen 153 in the base end direction. At this time, the distal end large-diameter portion 531 gets caught on the sub-through-hole 423 of the intermediate member 40 to be restricted from moving in the base end direction. Therefore, the distal end flexible portion 10A of the shaft 10 warps in the direction indicated by arrow A3 of FIG. 3A, and the distal end of the endoscope 100 (the distal end tip 30) deflects in the same direction.

By rotating the operation knob 26 in the other direction and pulling the base end of the operation wire 54, the operation wire 54 moves the wire lumen 154 in the base end direction. At this time, the distal end large-diameter portion 541 gets caught on the sub-through-hole 424 of the intermediate member 40 to be restricted from moving in the base end direction. Therefore, the distal end flexible portion 10A of the shaft 10 warps in the direction indicated by arrow A4 of FIG. 3A, and the distal end of the endoscope 100 (the distal end tip 30) deflects in the same direction.

When the tail ends of the operation wires 51, 52, 53, 54 are pulled as described above, the distal end large-diameter portions 511, 521, 531, 541 get caught on the sub-through-holes 421, 422, 423, 424 formed in the intermediate member 40, and the distal ends of the operation wires 51, 52, 53, 54 are fixed to the distal end of the shaft 10 (are prevented from being removed), and thus the distal end flexible portion 10A of the shaft 10 can be warped in the desired direction (the directions indicated by arrows A1 to A4).

The intermediate member is not disposed between the shaft and the distal end tip. In such a case, when the base end of the operation wire is pulled, the distal end of the operation wire (the distal end large-diameter portion) cannot be sufficiently fixed with respect to the distal end of the shaft (prevented from being removed), and the distal end large-diameter portion moves in the base end direction while pushing and expanding the wire lumen. In this case, the distal end flexible portion cannot be warped.

The constituent material of the operation wires 51, 52, 53, 54 is not particularly limited, and the same material as the constituent material of operation wires used in a conventionally known medical device that can perform distal end deflection operation can be used.

The camera 60 constituting the endoscope 100 includes a camera head 61 on which a CMOS image sensor 611 is mounted, a cable tube 65 contains a transmission cable of the CMOS image sensor 611, and optical fibers (not illustrated) are built in the camera 60 to surround the CMOS image sensor 611.

The outer diameter of the camera head 61 is preferably from 0.5 to 2.9 mm, and is 1.0 mm as one preferred example. The outer diameter of the cable tube 65 is substantially equal to the outer diameter of the camera head 61.

The camera 60 is disposed in the camera channels (the camera channel 13 and the camera channel 33) of the shaft 10 and the distal end tip 30. A base end portion of the cable tube 65 protrudes out from the camera channel port 23 of the handle 20, and a base end of the cable tube is connected to a control device.

A camera connector 70 is attached to the cable tube 65 of the camera 60.

The camera connector 70 is mounted to the camera channel port 23 of the handle 20 when the camera 60 is properly disposed in the camera channel 13 and the camera channel 33.

In other words, by mounting the camera connector 70 to the camera channel port 23, the camera 60 is properly disposed in the camera channel 13 and the camera channel 33.

The mounting position of the camera connector 70 is 300 to 5000 mm from a distal end of the camera 60, and is 2100 mm from the distal end of the camera 60 as one preferred example.

In the endoscope 100 of the present embodiment, the camera 60 is separable from the handle 20 and the shaft 10.

In other words, the camera connector 70 is removed from the camera channel port 23, and then the camera 60 disposed in the camera channel 13 and the camera channel 33 can be removed from the camera channel port 23 of the handle 20 along with the camera connector 70.

Also, once separated, the camera 60 can be reincorporated as a component of the endoscope 100 by inserting, with the camera head 61 first, the camera 60 into the handle 20 and the camera channel 13 of the shaft 10, from the camera channel port 23 of the handle 20, and mounting the camera connector 70 to the camera channel port 23.

The camera connector 70 includes a camera position adjustment mechanism that allows the camera 60 to reciprocate with respect to the camera channel 13 and the camera channel 33 such that a distal end of the camera 60 disposed in the camera channel 13 and the camera channel 33 shifts between a first position (a distal end position of the camera 60 as illustrated in FIG. 6A) located further on the base end side than the distal end surface 35 of the distal end tip 30 into which the camera channel 33 opens and a second position (a distal end position of the camera 60 as illustrated in FIG. 6B) located further on the distal end side than the distal end surface 35 when mounted to the camera channel port 23.

Here, the distance from the first position to the second position (the movement distance of the distal end of the camera 60 by the position adjustment mechanism) is preferably 2 to 100 mm, and is 30 mm as one preferred example.

In addition, the distance from the distal end surface 35 of the distal end tip 30 to the first position is preferably 1.5 to 20 mm, and the distance from the distal end surface 35 to the second position is preferably 0.5 to 80 mm.

In the endoscope 100 of the present embodiment, the camera position adjustment mechanism included in the camera connector 70 is a mechanism that reciprocates the camera 60 by using a feed screw.

Specifically, the mechanism includes: a connector case 71 that is mounted to the camera channel port 23 and in which guide grooves 712 extending in the axial direction are formed on an inner peripheral surface and in which a guide hole 713 extending in the axial direction is formed in a peripheral wall; a slide member 72 slidable to the connector case 71, the slide member 72 including a shaft portion 721 and a guide portion 723, the shaft portion 721 being a portion extending within the connector case 71 and partially protruding toward the base end side of the connector case 71, having a base end portion on which an external threaded portion 722 is formed, and into which the cable tube 65 of the camera 60 is inserted and adhesively fixed, the guide portion 723 being a portion integrally formed with the shaft portion 721 to surround a distal end portion of the shaft portion 721 and in which projected portions 724 to be guided by the guide grooves 712 of the connector case 71 are formed on an outer peripheral surface and in which a protruded portion 725 to be guided by the guide hole 713 is formed on the outer peripheral side; and a rotation knob 73 located on the base end side of the connector case 71 to be restricted from moving in the axial direction, the rotation knob 73 including an internal threaded portion 731 that screws with the external threaded portion 721 of the shaft portion 721 of the slide member 72. By rotating the rotation knob 73 in one direction to slide the slide member 72 from a base end position to a distal end position, the distal end of the camera 60 is moved from the first position (the distal end position of the camera 60 as illustrated in FIG. 6A) to the second position (the distal end position of the camera 60 as illustrated in FIG. 6B). By rotating the rotation knob 73 in the other direction to slide the slide member 72 from the distal end position to the base end position, the distal end of the camera 60 is moved from the second position to the first position.

Here, the "base end position" is a position in which the slide member 72 cannot move from the position thereof toward the base end side as illustrated in FIG. 5A, and the "distal end position" is a position in which the slide member 72 cannot move from the position thereof toward the distal end side as illustrated in FIG. 5B.

The camera position adjustment mechanism includes the connector case 71, the slide member 72, and the rotation knob 73.

The connector case 71 is a constituent member of the camera connector 70 mounted to the camera channel port 23 via a port-side connector described below, and includes a cylindrical body having an arch-shaped portion.

The guide grooves 712 extending in the axial direction are formed on the inner peripheral surface of the connector case 71, and the guide hole 713 extending in the axial direction is formed in the peripheral wall of the arch-shaped portion.

The slide member 72 includes the shaft portion 721 and the guide portion 723 integrally formed with the shaft portion 721 to surround the distal end portion of the shaft portion 721.

The shaft portion 721 of the slide member 72 extends within the connector case 71, and a portion of the shaft portion 721 protrudes out from an opening formed in a base end surface 711 of the connector case 71 toward the base end side.

The external threaded portion 722 is formed on the base end portion of the shaft portion 721.

As illustrated in FIGS. 5A and 5B, the cable tube 65 of the camera 60 is adhesively fixed inside the shaft portion 721 while being inserted thereinto.

The guide portion 723 of the slide member 72 has an arch-shaped portion along with the shape of the connector case 71, and is integrally formed with the shaft portion 721 to surround the distal end portion of the shaft portion 721.

The projected portions 724 to be guided by the guide grooves 712 of the connector case 71 are formed on the outer peripheral surface of the guide portion 723.

Additionally, the protruded portion 725 to be guided by the guide hole 713 of the connector case 71 is formed on the outer peripheral side of the arch-shaped portion of the guide portion 723.

The rotation knob 73 is disposed on the base end side of the connector case 71.

The internal threaded portion 731 that screws with the external threaded portion 722 of the shaft portion 721 of the slide member 72 is formed on the inner circumferential side of the rotation knob 73.

The rotation knob 73 is restricted from moving in the axial direction with respect to the connector case 71. By rotating the rotation knob 73, the slide member 72 slides with respect to the connector case 71.

Additionally, by rotating the rotation knob 73 to slide the slide member 72, the cable tube 65 adhesively fixed inside the shaft portion 721 also moves in the axial direction with respect to the connector case 71.

According to the camera position adjustment mechanism configured as described above, by rotating the rotation knob 73 in one direction to slide the slide member 72 from the base end position (the position illustrated in FIG. 5A) to the distal end position (the position illustrated in FIG. 5B), the distal end of the camera 60 can be moved from the first position (the distal end position of the camera 60 as illustrated in FIG. 6A) to the second position (the distal end position of the camera 60 as illustrated in FIG. 6B). By rotating the rotation knob 73 in the other direction to slide the slide member 72 from the distal end position to the base end position, the distal end of the camera 60 can be moved from the second position to the first position.

In the camera position adjustment mechanism as described above, in a case where the camera connector 70 is mounted to the camera channel port 23 when the slide member 72 is not at the base end position, the distal end of the camera 60 is likely to protrude out from the opening of the camera channel 33 in the distal end surface 35 of the distal end tip 30.

When attempting to insert the shaft 10 into the body in a state where the distal end of the camera 60 protrudes out from the opening of the camera channel 33, body tissue may be damaged by the distal end of the camera 60, or the inside of a channel of a delivery device (e.g., a master endoscope such as a duodenoscope) for guiding the camera 60 (the camera head 61) to a location close to a target section may be damaged by the distal end of the camera 60, or the camera 60 itself may be damaged.

Therefore, the endoscope 100 of the present embodiment includes a connector mounting restriction mechanism that restricts the camera connector 70 from being mounted to the camera channel port 23 when the slide member 72 is not at the base end position (when the distal end of the camera 60 possibly protrudes out from the opening of the camera channel 33).

The connector mounting restriction mechanism is configured to include a port-side connector 80 mounted to the camera channel port 23 to be interposed between the camera channel port 23 and the camera connector 70.

A distal end portion 81 of the port-side connector 80 is inserted from the camera channel port 23 into the handle 20.

A base end portion 82 of the port-side connector 80 includes an inner tube portion 821 that forms an insertion path for the shaft portion 721 of the slide member 72 (the cable tube 65 adhesively fixed into the shaft portion 721), and an outer tube portion 822 that has an outer peripheral shape formed to match an inner peripheral shape of the connector case 71.

In a peripheral wall of the outer tube portion 822, cut portions 823 to 826 are formed to avoid contact with the projected portions 724 formed on the guide portion 723 when the slide member 72 slides, and a cut portion 827 is formed to avoid contact with the protruded portion 725 formed on the guide portion 723 when the slide member 72 slides. Also, a hemispherical projection 829 is formed on the outer peripheral side of a peripheral wall portion 828 that is sandwiched between the cut portions 824 and 825 to have flexibility.

On the other hand, the peripheral wall of the connector case 71 is provided with a circular through-hole 715 into which the projection 829 fits when the base end portion 82 of the port-side connector 80 is inserted into the connector case 71.

According to the connector mounting restriction mechanism configured as just described, when attempting to insert the base end portion 82 of the port-side connector 80 into the connector case 71 in order to connect the port-side connector 80 to the camera connector 70 when the slide member 72 is at the base end position, the peripheral wall portion 828 is warped to retract the projection 829 inward such that the projection 829 does not disturb the insertion. In addition, when the base end portion 82 of the port-side connector 80 is inserted into the connector case 71, the warped peripheral wall portion 828 returns to the original posture as illustrated in FIG. 9A, and the projection 829 is fitted into the through-hole 715 of the connector case 71. As a result, the port-side connector 80 and the camera connector 70 are connected, and the camera connector 70 is mounted via the port-side connector 80 to the camera channel port 23.

Even when attempting to insert the base end portion 82 of the port-side connector 80 into the connector case 71 when the slide member 72 is not at the base end position, as illustrated in FIG. 9B, a distal end of the slide member 72 interferes with the peripheral wall portion 828 warped inward and thus the base end portion 82 of the port-side connector 80 cannot be inserted into the connector case 71. Therefore, the camera connector 70 cannot be connected to the port-side connector 80, and the camera connector 70 cannot be mounted to the camera channel port 23.

According to the endoscope 100 of the present embodiment, the distal ends of the operation wires 51, 52, 53, 54 can be securely fixed to the distal end of the shaft 10 by the intermediate member 40 that is made of metal and is disposed between the shaft 10 and the distal end tip 30. In other words, when the tail ends of the operation wires 51, 52, 53, 54 are pulled, the distal end large-diameter portions 511, 521, 531, 541 get caught on the sub-through-holes 421, 422, 423, 424 of the intermediate member 40. Therefore, the movement of the distal ends of the operation wires 51, 52, 53, 54 in the base end direction can be restricted. Thus, the distal end flexible portion 10A of the shaft 10 can be reliably warped in the desired direction.

Further, the outer diameter of the intermediate member 40 is equal to the outer diameters of the shaft 10 and the distal end tip 30, and thus the outer circumferential surface of the shaft 10, the outer circumferential surface of the intermediate member 40, and the outer circumferential surface of the distal end tip 30 are flush with one another. Therefore, the intermediate member 40 does not protrude from between the shaft 10 and the distal end tip 30 and the edge thereof is not exposed, and thus body tissue and the like are not damaged by the edge of the intermediate member 40.

Furthermore, since the intermediate member 40 is formed in a disk shape and located at the distal end of the shaft 10, the entire distal end flexible portion 10A of the shaft 10 can be warped and smooth deflection operation can be performed, unlike known endoscopes configured such that a distal end of an operation wire is fixed by a cylindrical metal member.

In addition, the shaft 10 and the distal end tip 30 are directly bonded on the inner side of the main through-hole 41 of the intermediate member 40 and on the outer side of each of the communication paths 43, 441, 442, 47 (in a region surrounded by the main through-hole 41 excluding the communication paths)(the constituent resins of the shaft and the distal end tip are welded). Therefore, the intermediate member 40 is also secured by the resin present on the inner side of the main through-hole 41, and a positional shift is not caused as the intermediate member 40 rotates about the axis of the shaft 10.

Moreover, the shaft 10 and the distal end tip 30 are directly bonded on the inner side of the main through-hole 41 of the intermediate member 40 and on the outer side of the communication paths 43, 441, 442, 47. Thus, although the intermediate member 40 made of metal is interposed between the shaft 10 and the distal end tip 30, the distal end tip 30 can be firmly secured to the shaft 10, and the distal end tip 30 does not fall off from the distal end of the shaft 10.

Further, each of the distal end large-diameter portions 511, 521, 531, 541 of the operation wires 51, 52, 53, 54 is embedded in the distal end tip 30, and thus, during pulling operation of the operation wire 51 or 52, the distal end of the operation wire 52 or 51 opposed to the operation wire 51 or 52 does not move (extend out) in the distal end direction. Also, during pulling operation of the operation wire 53 or 54, the distal end of the operation wire 54 or 53 opposed to the operation wire 53 or 54 does not move (extend out) in the distal end direction.

Furthermore, since the disk-shaped intermediate member 40 is mounted differently from a case where a cylindrical metal member is mounted, it is not necessary to cut the outer circumference of the shaft 10. Therefore, even when the shaft 10 has a small diameter, the diameter of the forceps channel 17 can be sufficiently secured.

Additionally, by separating, from the handle and the shaft, the camera 60 having an expensive solid state image sensor and washing the camera 60 after use, the camera 60 can be incorporated and reused as a component of the endoscope 100.

Further, with the camera position adjustment mechanism and the connector mounting restriction mechanism, the shaft 10 can be reliably prevented from being inserted into a delivery device or body in a state where the camera 60 protrudes out from the opening of the camera channel 33 in the distal end surface 35 of the distal end tip 30.

Furthermore, the distal end position of the camera 60 with respect to the distal end surface 35 of the distal end tip 30 can be finely adjusted by the camera position adjustment mechanism that reciprocates the camera 60 by using a feed screw.

Second Embodiment

FIG. 10 is an explanatory diagram illustrating a distal end portion of an endoscope 200 according to a second embodiment of the medical device of the present invention, and FIG. 11 illustrates a cross-section taken along the line XI-XI of FIG. 10.

In FIGS. 10 and 11, the same reference numerals are used for the same components as those of the endoscope 100 according to the first embodiment.

The endoscope 200 of the present embodiment includes a shaft 10, a handle 20, a distal end tip 30, operation wires 51, 52, 53, 54, and a camera 60 that are similar to the shaft 10, the handle, the distal end tip 30, the operation wires 51, 52, 53, 54, and the camera 60 that constitute the endoscope 100 according to the first embodiment.

The outer diameters of the shaft 10 and the distal end tip 30 that constitute the endoscope 200 are equal to each other; however, the outer diameter of an intermediate member 45 that constitutes the endoscope 200 is slightly smaller than the outer diameters of the shaft 10 and the distal end tip 30.

The outer diameter of the intermediate member 45 is preferably from 1.0 to 12.95 mm, and is 3.4 mm as one preferred example.

Here, the outer diameter of the shaft 10 is ($D_{10}$) and the outer diameter of the intermediate member 45 is ($D_{45}$), with ($D_{45}/D_{10}$) preferably being 0.8 to 0.99, and 0.97 (3.4 mm/3.5 mm) as one preferred example.

Also, ($D_{10}$-$D_{45}$) is preferably 0.05 to 3 mm, and is 0.1 mm (3.5 mm-3.4 mm) as one preferred example.

Due to the difference in outer diameter, a step with the size of ($D_{10}$-$D_{45}$)/2 is generated between the outer circumferential surface of the intermediate member 45 and the outer circumferential surface of the shaft 10 and between the outer circumferential surface of the intermediate member 45 and the outer circumferential surface of the distal end tip 30. However, as illustrated in FIGS. 10 and 11, a coating resin layer 135 is formed on the outer circumference of the intermediate member 45 so as to eliminate this step.

As a result, the outer circumferential surface of the shaft 10, the outer circumferential surface of the coating resin layer 135, and the outer circumferential surface of the distal end tip 30 are flush with one another.

According to the endoscope 200 of the present embodiment, in addition to achieving the same effect as the effect of the endoscope 100 according to the first embodiment, the edge of the intermediate member 45 can be prevented from being exposed even in a case where a slight positional shift in a radial direction of the intermediate member 45 with respect to the shaft 10 and the distal end tip 30 is caused, for example, by repeated pulling operation.

Third Embodiment

A steerable sheath according to a third embodiment of the medical device of the present invention will be described.

A steerable sheath 300 of the present embodiment illustrated in FIGS. 12 to 16 is a device for introducing a sheath shaft 310 into the body prior to insertion of a catheter (not illustrated) or the like into the body of a patient.

The steerable sheath 300 of this embodiment includes: the sheath shaft 310 in which a lumen (working lumen) 317 extending along a central axis of the distal end flexible portion and two wire lumens 3151, 3152 disposed opposed to each other with the lumen 317 interposed therebetween are formed, the sheath shaft 310 being made of resin and including a distal end flexible portion 310A; a handle 320 disposed on a base end side of the sheath shaft 310 and provided with a rotational operation portion 322; a distal end tip 330 made of resin, disposed on a distal end side of the sheath shaft 310, and having, at least on a base end thereof, an outer diameter equal to that of the sheath shaft 310, the distal end tip 330 in which a lumen 337 (a distal end working lumen) in communication with the lumen 317 of the sheath shaft 310 and open at a distal end surface 335 of the distal end tip is formed; an intermediate member 340 made of metal, disposed between the sheath shaft 310 and the distal end tip 330, and formed in a disk shape having an outer diameter equal to that of the sheath shaft 310, the intermediate member 340 including a main through-hole 346 that has a circular shape and is formed to ensure a communication path 345 with the lumen 317 of the sheath shaft 310 and the lumen 337 of the distal end tip 330 and surround the communication path 345, and two sub-through-holes 3471, 3472 that are formed to correspond to the positions in which the wire lumens 3151, 3152 are formed; a first operation wire 351 serving as an operation wire for deflecting a distal end of the sheath shaft 310 in a first direction D1, including a distal end large-diameter portion 3511 that is embedded in the distal end tip 330 and has a diameter larger than a diameter of the sub-through-hole 3471 of the intermediate member 340, passing through the sub-through-hole 3471 and extending in the wire lumen 3151 of the sheath shaft 310, and having a tail end that can be pulled by rotating the rotational operation portion 322 of the handle 320 in one direction (a clockwise direction); and a second operation wire 352 serving as an operation wire for deflecting the distal end of the sheath shaft 310 in a second direction D2, including a distal end large-diameter portion 3521 that is embedded in the distal end tip 330 and has a diameter larger than a diameter of the sub-through-hole 3472 of the intermediate member 340, passing through the sub-through-hole 3472 and extending in the wire lumen 3152 of the sheath shaft 310, and having a tail end that can be pulled by rotating the rotational operation portion 322 of the handle 320 in the other direction (a counterclockwise direction). The sheath shaft 310 and the distal end tip 330 are directly bonded on the inner side of the main through-hole 346 of the intermediate member 340 and on the outer side of the communication path 345 (the constituent resins of the shaft and the distal end tip are welded).

In FIGS. 12 and 16, a branch tube (side arm) is indicated by 381 and a three-way stopcock is indicated by 382.

The steerable sheath 300 includes the sheath shaft 310 to be introduced into the body, the handle 320 disposed on the base end side of the sheath shaft 310, the distal end tip 330 disposed on the distal end side of the sheath shaft 310, the intermediate member 340 disposed between the sheath shaft 310 and the distal end tip 330, the first operation wire 351 extending in the wire lumen 3151 of the sheath shaft 310, and the second operation wire 352 extending in the wire lumen 3152 of the sheath shaft 310.

As illustrated in FIGS. 13 and 14A, the lumen 317 extending along the central axis of the sheath shaft 310 is formed, in the sheath shaft 310 constituting the steerable sheath 300, as a working lumen that serves as an insertion path for a medical device such as a catheter.

Additionally, the wire lumen 3151 that is an insertion path for the first operation wire 351 and the wire lumen 3152 that is an insertion path for the second operation wire 352 are formed in the sheath shaft 310.

The length (effective length) of the sheath shaft 310 is preferably 200 to 1500 mm, and is 700 mm as one preferred example.

The sheath shaft 310 includes the distal end flexible portion 310A.

The length of the distal end flexible portion 310A is preferably 10 to 150 mm, and is 50 mm as one preferred example.

The outer diameter of the sheath shaft 310 is preferably 2 to 5 mm, and is 4 mm as one preferred example.

The inner diameter of the sheath shaft 310 (the diameter of the lumen 317) is preferably 1 to 4 mm, and is 3 mm as one preferred example.

The sheath shaft 310 is made of resin.

Examples of the resin material constituting the sheath shaft 310 can include nylon resin, polyether block amide (PEBAX) resin, polyurethane resin, polyolefin resin, and the like, and of these resins, PEBAX resin is preferable.

The hardness (Shore D hardness) of the constituent resin of the sheath shaft 310 is preferably 90 D or less, and when one preferred example is given, the hardness of the resin forming the distal end flexible portion 310A is 25 D, and the hardness of the resin forming a portion other than the distal end flexible portion 310A is 75 D.

The distal end tip 330 is disposed on the distal end side of the shaft 10.

As illustrated in FIGS. 13 and 14B, the lumen 337 in communication with the lumen 317 of the sheath shaft 310 and extending along the central axis of the distal end tip 330 to open at the distal end surface 335 of the distal end tip 330 is formed, in the distal end tip 330 constituting the steerable sheath 300, as a distal end working lumen that serves as an insertion path for a medical device.

The lumen 337 of the distal end tip 330 is in communication with the lumen 317 of the sheath shaft 310 via the communication path 345 described below.

The diameter of the lumen 337 is equal to the diameter of the lumen 317 in communication with the lumen 337.

The length of the distal end tip 330 is preferably 1 to 10 mm, and is 5 mm as one preferred example.

The outer diameter at the base end of the distal end tip 330 is equal to the outer diameter of sheath shaft 310.

The distal end tip 330 is made of resin.

Examples of the resin material forming the distal end tip 330 can include resins similar to those illustrated as the resins forming the sheath shaft 310, and out of the resins, PEBAX resin is preferable.

The distal end tip 330 is made of a resin material having low hardness. The hardness (Shore D hardness) of the constituent resin of the distal end tip 330 is preferably 72 D or less, and is 35 D as one preferred example.

The intermediate member 340 formed in a disk shape (in an annular shape due to the formation of the main through-hole 346 described below) is disposed between the sheath shaft 310 and the distal end tip 330.

The intermediate member 340 constituting the steerable sheath 300 is a member for fixing a distal end of each of the first operation wire 351 and the second operation wire 352 to the distal end of the sheath shaft 310 (for preventing removal of the tail end during pulling operation).

As illustrated in FIG. 14C, the main through-hole 346 surrounding the communication path 345 is formed in the intermediate member 340.

Here, the communication path 345 is a path defined and formed by a constituent resin 3130 of the sheath shaft 310 and/or the distal end tip 330 in order to allow the lumen 317 of the sheath shaft 310 and the lumen 337 of the distal end tip 330 to communicate with each other. The diameter of the communication path 345 is equal to the diameters of the lumen 317 and the lumen 337.

In order to allow the sheath shaft 310 and the distal end tip 330 to be bonded on the inner side of the main through-hole 346, the diameter of the main through-hole 346 is larger than the diameter of the communication path 345.

Here, the diameter of the main through-hole 346 is preferably 1 to 5 mm, and is 3.4 mm as one preferred example.

In the intermediate member 340, the sub-through-hole 3471 is formed to correspond to the position in which the wire lumen 3151 of the sheath shaft 310 is formed and the sub-through-hole 3472 is formed to correspond to the position in which the wire lumen 3152 is formed.

The sub-through-hole 3471 and the sub-through-hole 3472 are insertion paths respectively for the first operation wire 351 and the second operation wire 352.

The diameters of the sub-through-hole 3471 and the sub-through-hole 3472 are larger than the diameters of the first operation wire 351 and the second operation wire 352 to be inserted and are adjusted to be smaller than the diameters of the distal end large-diameter portion 3511 and the distal end large-diameter portion 3521 intended to restrict insertion, but are preferably 0.05 to 3.0 mm and are 0.25 mm as one preferred example.

The thickness of the intermediate member 340 is preferably 0.05 to 3 mm, and is 0.15 mm as one preferred example.

The outer diameter of the intermediate member 340 is equal to the outer diameters of sheath shaft 310 and the distal end tip 330. The outer circumferential surface of the sheath shaft 310, the outer circumferential surface of the intermediate member 340, and the outer circumferential surface of the distal end tip 330 are flush with one another. Accordingly, the intermediate member 340 does protrude from between the sheath shaft 310 and the distal end tip 330 and the edge thereof is not exposed, and thus body tissue and the like are not damaged by such an edge.

Note that the outer diameter of the intermediate member is set to be slightly smaller than the outer diameters of the sheath shaft 310 and the distal end tip 330, and a coating resin layer may be formed on the outer circumference of such an intermediate member to eliminate or mitigate the step caused by the difference in outer diameter.

The intermediate member 340 is made of metal or ceramic, and is preferably made of metal.

Example of the metal material forming the intermediate member 340 can include stainless copper, platinum, gold, copper, nickel, titanium, tantalum, and the like, and of the metals, stainless copper is preferable.

The handle 320 is disposed on the base end side of the sheath shaft 310.

The handle 320 that constitutes the steerable sheath 300 includes: a housing 321 into which a base end portion of the sheath shaft 310 is inserted; the rotational operation portion 322 disposed rotationally around a longitudinal axis of the housing 321 on a distal end side thereof; a rotation shaft 323 disposed inside the housing 321 to rotate in an operation direction of the rotational operation portion 322, the rotation shaft 323 being provided in the same region (a threaded portion) on an outer circumferential surface thereof with a right-hand thread and a left-hand thread; a first slider 3241 provided with a thread screwable with one of the right-hand thread and the left-hand thread of the rotation shaft 323, located in a home position when the distal end flexible portion 310A of the sheath shaft 310 is in a linear state and configured to, when the rotational operation portion 322 is rotated from this state in the clockwise direction, move from the home position in the base end direction along the rotation shaft 323 and to, when the rotational operation portion 322 is rotated from this state in the counterclockwise direction, move from the home position in the distal end direction along the rotation shaft 323; a second slider 3242 provided with a thread screwable with the other of the right-hand thread and the left-hand thread of the rotation shaft 323, located in a home position when the distal end flexible portion 310A of the sheath shaft 310 is in the linear state and configured to, when the rotational operation portion 322 is rotated from this state in the clockwise direction, move from the home position in the distal end direction along the rotation shaft 323 by a distance equal to the movement distance of the first slider 3241 and to, when the rotational operation portion 322 is rotated from the state in the counterclockwise direction, move from the home position in the base end direction along the rotation shaft 323 by a distance equal to the movement distance of the first slider 3241; a first anchor 3251 disposed to be contactable with the first slider 3241 on a base end side of the first slider 3241, fixed to a base end portion of the first operation wire 351 for deflecting the distal end of the sheath shaft 310 in the first direction $D_1$, located in a neutral position when the distal end flexible portion 310A of the sheath shaft 310 is in the linear state, movable from the neutral position in the distal end direction and the base end direction, and configured to, when the first slider 3241 moves in the base end direction, move in the base end direction along the rotation shaft 323 while being in contact with the first slider 3241; and a second anchor 3252 disposed to be contactable with the second slider 3242 on a base end side of the second slider 3242, fixed to a base end portion of the second operation wire 352 for deflecting the distal end of the sheath shaft 310 in the second direction $D_2$, located in a neutral position when the distal end flexible portion 310A of the sheath shaft 310 is in the linear state, movable from the neutral position in the distal end direction and the base end direction, and configured to, when the second slider 3242 moves in the base end direction, move in the base end direction along the rotation shaft 323 while being in contact with the second slider 3242.

The handle 320 includes the housing 321, the rotational operation portion 322, the rotation shaft 323, the first slider 3241, the second slider 3242, the first anchor 3251, and the second anchor 3252.

The base end portion of the sheath shaft 310 is inserted into the housing 321 that constitutes the handle 320.

The rotational operation portion 322 that constitutes the handle 320 is a dial that is disposed on the distal end side of the housing 321 and that can rotate about the longitudinal axis of the housing 321.

The rotation shaft 323 disposed inside the housing 321 and constituting the handle 320 is fixed to a rotation shaft of the rotational operation portion 322, and by operating the rotational operation portion 322, the rotation shaft 323 rotates in the same direction as the operation direction. The right-hand thread and the left-hand thread that have an equal lead to each other are formed in the same region (threaded portion) on the outer circumferential surface of the rotation shaft 323.

As illustrated in FIG. 12, when the distal end flexible portion 310A of the sheath shaft 310 is in the linear state, the first slider 3241 and the second slider 3242 are both located in the home position (the same position with each other in the axial direction).

Note that the dotted line 3245 in FIGS. 12 and 16 indicates a base end position of the first slider 3241 and the second slider 3242 when the sliders are located in the home position.

The first slider 3241 that constitutes the handle 320 includes, on the distal end side, a gutter-shaped portion 3246 having an inner circumferential surface on which a thread screwable with one of the right-hand thread and the left-hand thread formed on the outer circumferential surface of the rotation shaft 323 is formed.

Also, the second slider 3242 that constitutes the handle 320 includes, on the distal end side, a gutter-shaped portion 3247 having an inner circumferential surface on which a thread screwable with the other of the right-hand thread and the left-hand thread formed on the outer circumferential surface of the rotation shaft 323 is formed.

The base end portion of the first operation wire 351 for deflecting the distal end of the sheath shaft 310 in the first direction D1 is fixed to the first anchor 3251 that is disposed on the base end side of the first slider 3241 and constitutes the handle 320.

The first operation wire 351 is inserted through the rotation shaft 323 into the housing 321 to be fixed to the first anchor 3251. Note that in FIGS. 12 and 16, the first operation wire 351 not actually visible behind the first slider 3241 is illustrated by the dotted line.

On the other hand, a distal end portion of the first operation wire 351 is fixed to a distal end portion of the sheath shaft 310.

The first anchor 3251 is disposed to be contactable with and separable from the first slider 3241 located on the distal end side of the first anchor 3251. In other words, the first anchor 3251 and the first slider 3241 are not fixed, and both can move in a contact manner with each other or in a separated manner from each other.

The base end portion of the second operation wire 352 for deflecting the distal end of the sheath shaft 310 in the second direction D2 is fixed to the second anchor 3252 that is disposed on the base end side of the second slider 3242 and constitutes the handle 320.

The second operation wire 352 is inserted through the rotation shaft 323 into the housing 321 to be fixed to the second anchor 3252. Note that in FIGS. 12 and 16, the second operation wire 352 not actually visible behind the second slider 3242 is illustrated by the dotted line.

On the other hand, a distal end portion of the second operation wire 352 is fixed to the distal end portion of the sheath shaft 310 (a circumferential position opposed to the fixed position of the distal end portion of the first operation wire 351).

The second anchor 3252 is disposed to be contactable with and separable from the second slider 3242 located on the distal end side of the second anchor 3252. In other words, the second anchor 3252 and the second slider 3242 are not fixed, and both can move in a contact manner with each other or in a separated manner from each other.

As illustrated in FIG. 12, when the distal end flexible portion 310A of the sheath shaft 310 is in the linear state, the first anchor 3251 and the second anchor 3252 are both located in the neutral position (the same position with each other in the axial direction).

Note that the dashed-dotted line 3255 in FIGS. 12 and 16 indicates a central position of the first anchor 3251 and the second anchor 3252 when the anchors are located in the neutral position.

The first anchor 3251 can move from the neutral position in the distal end direction and the base end direction as long as the movement of the first anchor 3251 in the distal end direction is not disturbed by the first slider 3241 stopped in the home position.

The first anchor 3251 moves in the base end direction while being in contact with the first slider 3241 (when being pushed by the first slider 3241), and moves in the distal end direction under pulling force from the first operation wire 351.

The second anchor 3252 can move from the neutral position in the distal end direction and the base end direction as long as the movement of the second anchor 3252 in the distal end direction is not disturbed by the second slider 3242 stopped in the home position.

The second anchor 3252 moves in the base end direction while being in contact with the second slider 3242 (when being pushed by the second slider 3242), and can move in the distal end direction under pulling force from the second operation wire 352.

The rotational operation portion 322 is rotated in the clockwise direction when the distal end flexible portion 310A of the sheath shaft 310 is in the linear state as illustrated in FIG. 12, and thereby the rotation shaft 323 is rotated in the same direction. Accordingly, the first slider 3241 configured such that the thread screwable with one of the threads formed on the outer circumferential surface of the rotation shaft 323 is formed on the inner circumferential surface of the gutter-shaped portion 3246 moves from the home position in the base end direction along the rotation shaft 323, and the second slider 3242 configured such that the thread screwable with the other of the threads formed on the outer circumferential surface of the rotation shaft 323 is formed on the inner circumferential surface of the gutter-shaped portion 3247 moves from the home position in the distal end direction along the rotation shaft 323.

Here, the distance (feed amount) in which the first slider 3241 moves in the base end direction and the distance (feed amount) in which the second slider 3242 moves in the distal end direction are equal to each other.

As the first slider 3241 moves in the base end direction, the first anchor 3251 located on the base end side of the first slider moves in the base end direction along the rotation shaft 323 (together with the first slider 3241) while being in contact with the first slider 3241.

The first anchor 3251 moves in the base end direction, and thus the base end portion of the first operation wire 351 is pulled. Accordingly, the distal end flexible portion 310A warps from the linear state in the first direction D1, and the distal end of the sheath shaft 310 deflects in the same direction.

At this time, the tensile force generated by deflecting the distal end flexible portion 310A of the sheath shaft 310 in the first direction D1 (tensile force in the distal end direction) acts on the second operation wire 352. However, the second slider 3242 moves from the home position in the distal end direction by a distance equal to the movement distance of the first slider 3241 (thus, the movement of the second anchor 3252 in the distal end direction is not disturbed by the second slider 3242), and the second anchor 3252 moves from the neutral position in the distal end direction in accordance with the tensile force acting on the second operation wire 352; therefore, the second operation wire 352 is pulled out. As a result, the tensile force acting on the second operation wire 352 can be canceled.

In addition, the second slider 3242 and the second anchor 3252 are contactable with and separable from each other. Accordingly, when the tensile force acting on the second operation wire 352 is canceled, the second anchor 3252 can be stopped without following the movement of the second slider 3242. Therefore, the second operation wire 352 can be prevented from being pulled out more than necessary. As a result, no slack is generated on the second operation wire 352 inside the housing 321.

The rotational operation portion 322 is rotated in the counterclockwise direction when the distal end flexible portion 310A of the sheath shaft 310 is in the linear state as illustrated in FIG. 12, and thereby the rotation shaft 323 is rotated in the same direction. Accordingly, the first slider 3241 configured such that the thread screwable with one of the threads formed on the outer circumferential surface of the rotation shaft 323 is formed on the inner circumferential surface of the gutter-shaped portion 3246 moves from the home position in the distal end direction along the rotation shaft 323, and the second slider 3242 configured such that the thread screwable with the other of the threads formed on the outer circumferential surface of the rotation shaft 323 is formed on the inner circumferential surface of the gutter-shaped portion 3247 moves from the home position in the base end direction along the rotation shaft 323.

Here, the distance (feed amount) in which the first slider 3241 moves in the distal end direction and the distance (feed amount) in which the second slider 3242 moves in the base end direction are equal to each other.

As the second slider 3242 moves in the base end direction, the second anchor 3252 located on the base end side of the second slider moves in the base end direction along the rotation shaft 323 (together with the second slider 3242) while being in contact with the second slider 3242.

The second anchor 3252 moves in the base end direction, and thus the base end portion of the second operation wire 352 is pulled. Accordingly, the distal end flexible portion 310A warps from the linear state in the second direction D2, and the distal end of the sheath shaft 310 deflects in the same direction.

At this time, the tensile force generated by deflecting the distal end flexible portion 310A of the sheath shaft 310 in the second direction D2 (tensile force in the distal end direction) acts on the first operation wire 351. However, the first slider 3241 moves from the home position in the distal end direction by a distance equal to the movement distance of the second slider 3242 (thus, the movement of the first anchor 3251 in the distal end direction is not disturbed by the first slider 3241), and the first anchor 3251 moves from the neutral position in the distal end direction in accordance with the tensile force acting on the first operation wire 351; therefore, the first operation wire 351 is pulled out. As a result, the tensile force acting on the first operation wire 351 can be canceled.

In addition, the first slider 3241 and the first anchor 3251 are contactable with and separable from each other. Accordingly, when the tensile force acting on the first operation wire 351 is canceled, the first anchor 3251 can be stopped without following the movement of the first slider 3241. Therefore, the first operation wire 351 can be prevented from being pulled out more than necessary. As a result, no slack is generated on the first operation wire 351 inside the housing 321.

FIG. 16 illustrates a state where the distal end flexible portion 310A of the sheath shaft 310 is warped in the second direction due to the movement of the second anchor 3252 in the base end direction along with the second slider 3242. In the state illustrated in the same drawing, the distance in which the second slider 3242 is moved from the home position in the base end direction is equal to the distance in which the second anchor 3252 is moved from the neutral position in the base end direction. Meanwhile, the distance in which the first slider 3241 is moved from the home position in the distal end direction is longer than the distance in which the first anchor 3251 is moved from the neutral position in the distal end direction (the distance that is required to cancel the tensile force acting on the first operation wire 351), and the first slider 3241 is separated from the first anchor 3251.

When the first slider 3241 and the first anchor 3251 cannot be separated, the first anchor 3251 follows the movement of the first slider 3241 and is moved in the distal end direction by the same distance as the movement distance of the first slider 3241. In such a case, the first operation wire 351 with the base end fixed to the first anchor 3251 is pulled out more than necessary and thus gets slack inside the housing 321. However, the first slider 3241 and the first anchor 3251 that constitute the handle 320 are disposed to be contactable with or separable from each other, and thus both can be separated. Consequently, no slack is generated on the first operation wire 351 inside the housing 321.

In the handle 320, for example, the housing 321 is held by the right hand, and the rotational operation portion 322 is rotated by the thumb and forefinger of the right hand, and thus the distal end flexible portion 310A is warped and the distal end of the sheath shaft 310 can be deflected.

Note that the mechanism by which the rotational operation portion is rotated to deflect the distal end flexible portion of the sheath shaft is obviously not limited to the aforementioned mechanism.

Further, in the steerable sheath 300 of the present embodiment, the rotational operation portion 322 constituting the handle 320 is disposed on the distal end side of the housing 321; however, the rotational operation portion may be disposed on the base end side of the housing.

Furthermore, the rotational operation portion may be configured to rotate about an axis orthogonal to the longitudinal direction of the handle (housing).

According to the steerable sheath 300 of the present embodiment, the distal end of the first operation wire 351 and the distal end of the second operation wire 352 can be securely fixed to the distal end of the sheath shaft 310 by the intermediate member 340 that is made of metal and is disposed between the sheath shaft 310 and the distal end tip 330. In other words, when the tail end of the first operation wire 351 is pulled, the distal end large-diameter portion 3511 gets caught on the sub-through-hole 3471 of the intermediate member 340, and the movement of the distal end of the first operation wire 351 in the base end direction is restricted, and when the tail end of the second operation wire 352 is pulled, the distal end large-diameter portion 3521 gets caught on the sub-through-hole 3472 of the intermediate member 340, and the movement of the distal end of the second operation wire 352 in the base end direction is restricted. As a result, the distal end flexible portion 310A of the sheath shaft 310 can be reliably warped in the desired direction (the first direction D1 or the second direction D2).

Further, the outer diameter of the intermediate member 340 is equal to the outer diameters of the sheath shaft 310 and the distal end tip 330, and thus the outer circumferential surface of the sheath shaft 310, the outer circumferential surface of the intermediate member 340, and the outer circumferential surface of the distal end tip 330 are flush with one another. Therefore, the intermediate member 340 does not protrude from between the sheath shaft 310 and the distal end tip 330 and the edge thereof is not exposed, and thus body tissue and the like are not damaged by the edge of the intermediate member 340.

Furthermore, since the intermediate member 340 is formed in a disk shape located at the distal end of the sheath shaft 310, the entire distal end flexible portion 10A of the sheath shaft 310 is warped and smooth deflection operation can be performed.

In addition, the sheath shaft 310 and the distal end tip 330 are directly bonded (both constituent resins are welded) on the inner side of the main through-hole 346 of the intermediate member 340 and on the outer side of the communication path 345. Accordingly, although the intermediate member 340 made of metal is interposed between the sheath shaft 310 and the distal end tip 330, the distal end tip 330 can be firmly secured to the sheath shaft 310, and the distal end tip 330 does not fall off from the distal end of the sheath shaft 310.

Moreover, in a case where the first operation wire 351 or the second operation wire 352 is pulled by rotationally operating the rotational operation portion 322, the tensile force acting on the second operation wire 352 or the first operation wire 351 that is not pulled can be canceled, and no slack is generated inside the housing 321 on the second operation wire 352 or the first operation wire 351 that is not pulled.

REFERENCE SIGNS LIST

100 Endoscope
10 Shaft
10A Distal end flexible portion
13 Camera channel
130 Constituent resin of shaft and/or distal end tip
141, 142 Water channel
151, 152, 153, 154 Wire lumen
17 Forceps channel
20 Handle
21 Grip
23 Camera channel port
25, 26 Operation knob
27 Forceps channel port
30 Distal end tip
35 Distal end surface of distal end tip
33 Camera channel
341, 342 Water channel
37 Forceps channel
40 Intermediate member
41 Main through-hole

421, 422, 423, 424 Sub-through-hole
43, 441, 442, 47 Communication path
51, 52, 53, 54 Operation wire
511, 521, 531, 541 Distal end large-diameter portion of
  operation wire
60 Camera
61 Camera head
611 CMOS image sensor
65 Cable tube
70 Camera connector
71 Connector case
711 Base end surface
712 Guide groove
713 Guide hole
715 Through-hole
72 Slide member
721 Shaft portion
722 External threaded portion
723 Guide portion
724 Projected portion
725 Protruded portion
73 Rotation knob
731 Internal threaded portion
80 Port-side connector
81 Distal end portion
82 Base end portion
821 Inner tube portion
822 Outer tube portion
823 to 827 Cut portion
828 Peripheral wall portion
829 Hemispherical projection
200 Endoscope
45 Intermediate member
135 Coating resin layer
300 Steerable sheath
310 Sheath shaft
310A Distal end flexible portion
317 Lumen (working lumen)
3130 Constituent resin of sheath shaft and/or distal end tip
3151, 3152 Wire lumen
320 Handle
321 Housing
322 Rotational operation portion
323 Rotation shaft
3241 First slider
3242 Second slider
3251 First anchor
3252 Second anchor
3246, 3247 Gutter-shaped portion
3245 Dotted line
3255 Dashed-dotted line
330 Distal end tip
335 Distal end surface of distal end tip
337 Lumen (distal end working lumen)
340 Intermediate member
345 Communication path
346 Main through-hole
3471, 3472 Sub-through-hole
351 First operation wire
3511 Distal end large-diameter portion of first operation
  wire
352 Second operation wire
3521 Distal end large-diameter portion of second operation wire
381 Branch tube
382 Three-way stopcock

The invention claimed is:

1. A medical device provided with a distal end deflection-operable shaft, the medical device comprising:
  the shaft, in which at least one working lumen and at least one wire lumen are formed, the shaft being made of resin and including a distal end flexible portion;
  a distal end tip that has, at least on a base end thereof, an outer diameter being 80% to 120% of the outer diameter of the shaft and in which at least one distal end working lumen each in communication with the corresponding one of the at least one working lumen of the shaft and open at a distal end surface of the distal end tip is formed, the distal end tip being made of resin and disposed on a distal end side of the shaft;
  an intermediate member made of metal or ceramic, disposed between the shaft and the distal end tip, and formed in a plate shape having an outer diameter being 80% to 100% of the outer diameter of the shaft, the intermediate member including a main through-hole and a sub-through-hole, wherein the main through-hole includes a communication path formed by the resins of the shaft and/or the distal tip to communicate the at least one working lumen of the shaft with the at least one distal end working lumen of the distal end tip, and the main through-hole surrounds the communication path, and the sub-through-hole is formed to correspond to a position in which the at least one wire lumen is formed; and
  an operation wire including a distal end large-diameter portion that is embedded in the distal end tip and has a diameter larger than a diameter of the sub-through-hole of the intermediate member, the operation wire passing through the sub-through-hole and extending in the at least one wire lumen of the shaft and including a tail end that can be pulled, wherein
  the shaft and the distal end tip are directly bonded on a region between the main through- hole and the communication path of the intermediate member;
  the distal end tip is made of resin with a hardness of 72D or less.

2. The medical device according to claim 1, wherein the diameters of the at least one working lumen of the shaft and the at least one distal end working lumen of the distal end tip are both 80% to 120% of the diameter of the communication path.

3. The medical device according to claim 1, wherein the shaft includes a plurality of the working lumens.

4. The medical device according to claim 3, wherein one main through-hole surrounding all of the communication paths is formed in the intermediate member.

5. The medical device according to claim 1, wherein the shaft includes one working lumen.

6. The medical device claim 1, wherein
  the outer diameter of the intermediate member is smaller than an outer diameter of the shaft and the outer diameter of the distal end tip, and
  an outer circumference of the intermediate member is covered by a resin coating such that a step between the shaft and the distal end tip due to the smaller outer diameter of the intermediate member is eliminated.

7. A medical device used as an endoscope and provided with a distal end deflection-operable shaft, the medical device comprising:
  the shaft, in which a camera channel, a water channel, and a forceps channel are formed as working lumens and in which four wire lumens are formed, the shaft being made of resin and including a distal end flexible portion;

a handle disposed on a base end side of the shaft and provided with a rotational operation portion;

a distal end tip in which a camera channel, a water channel, and a forceps channel are formed as distal end working lumens that are respectively in communication with the working lumens of the shaft and are open at a distal end surface of the distal end tip, the distal end tip being made of resin, disposed on a distal end side of the shaft, and having an outer diameter being 80% to 120% of the outer diameter of the shaft;

an intermediate member made of metal or ceramic, disposed between the shaft and the distal end tip, and formed in a plate shape having an outer diameter being 80% to 100% of the outer diameter of the shaft, the intermediate member including a main through-hole and four sub-through-holes, wherein the main through-hole includes communication paths respectively formed by the resins of the shaft and/or the distal tip to communicate the working lumens of the shaft with the distal end working lumens of the distal end tip, and the main through-hole surrounds all of the communication paths, and the four sub-through-holes are formed to correspond to positions in which the wire lumens are formed; and four operation wires including distal end large-diameter portions that are embedded in the distal end tip and have diameters larger than diameters of the sub-through-holes of the intermediate member, the operation wires respectively passing through the sub-through-holes and respectively extending in the wire lumens of the shaft, and including respective tail ends that are fixed to the rotational operation portion of the handle and thereby can be pulled, wherein the shaft and the distal end tip are directly bonded on a region between the main through-hole and each of the communication paths of the intermediate member;

the distal end tip is made of resin with a hardness of 72D or less.

8. A medical device used as a steerable sheath and provided with a distal end deflection-operable shaft, the medical device comprising:

the shaft, in which one working lumen extending along a central axis of a distal end flexible portion and two wire lumens disposed opposed to each other with the working lumen interposed therebetween are formed, the shaft being made of resin and including the distal end flexible portion;

a handle disposed on a base end side of the shaft and provided with a rotational operation portion;

a distal end tip that has, at least on a base end thereof, an outer diameter being 80% to 120% of the outer diameter of the shaft and in which a distal end working lumen in communication with the working lumen of the shaft and open at a distal end surface of the distal end tip is formed, the distal end tip being made of resin and disposed on a distal end side of the shaft;

an intermediate member made of metal or ceramic, disposed between the shaft and the distal end tip, and formed in a plate shape having an outer diameter being 80% to 100% of the outer diameter of the shaft, the intermediate member including a main through-hole and two sub-through-holes, wherein the main through-hole includes a communication path formed by the resins of the shaft and/or the distal tip to communicate the working lumen of the shaft with the distal end working lumen of the distal end tip, and the main through-hole surrounds the communication path, and the two sub-through-holes are formed to correspond to positions in which the wire lumens are formed; and two operation wires including distal end large-diameter portions that are embedded in the distal end tip and have diameters larger than diameters of the sub-through-holes of the intermediate member, the operation wires respectively passing through the sub-through-holes and respectively extending in the wire lumens of the shaft, and including respective tail ends that can be pulled by rotating the rotational operation portion of the handle, wherein the shaft and the distal end tip are directly bonded on a region between the main through- hole and the communication path of the intermediate member;

the distal end tip is made of resin with a hardness of 72D or less.

* * * * *